(12) United States Patent
Janssens et al.

(10) Patent No.: US 7,435,736 B2
(45) Date of Patent: Oct. 14, 2008

(54) SUBSTITUTED 1-PIPERIDIN-4-YL-4-AZETIDIN-3-YL-PIPERAZINE DERIVATIVES AND THEIR USE AS NEUROKININ ANTAGONISTS

(75) Inventors: Frans Eduard Janssens, Bonheide (BE); François Maria Sommen, Wortel (BE); Benoît Christian Albert Ghislain De Boeck, Genval (BE); Joseph Elisabeth Leenaerts, Rijkevorsel (BE)

(73) Assignee: Janssen Pharmaceutica, N.V., Beerse (BE)

( * ) Notice: Subject to any disclaimer, the term of this patent is extended or adjusted under 35 U.S.C. 154(b) by 450 days.

(21) Appl. No.: 10/540,304

(22) PCT Filed: Dec. 17, 2003

(86) PCT No.: PCT/EP03/51042

§ 371 (c)(1),
(2), (4) Date: Jun. 21, 2005

(87) PCT Pub. No.: WO2004/056800

PCT Pub. Date: Jul. 8, 2004

(65) Prior Publication Data

US 2006/0074069 A1 Apr. 6, 2006

(30) Foreign Application Priority Data

Dec. 23, 2002 (WO) ............... PCT/EP02/14837

(51) Int. Cl.
*A61K 31/496* (2006.01)
*A61K 31/497* (2006.01)
*C07D 401/12* (2006.01)
*C07D 401/14* (2006.01)
*C07D 409/14* (2006.01)
*C07D 417/14* (2006.01)
*C07D 405/14* (2006.01)

(52) U.S. Cl. ............... 514/252.11; 514/253.11; 514/253.13; 544/357; 544/364

(58) Field of Classification Search ............... None
See application file for complete search history.

(56) References Cited

U.S. PATENT DOCUMENTS

| 5,310,743 | A | 5/1994 | Schilling et al. ............ 514/311 |
| 5,541,195 | A | 7/1996 | Schilling et al. ............ 514/311 |
| 5,646,144 | A | 7/1997 | Schilling et al. ............ 514/241 |

FOREIGN PATENT DOCUMENTS

| EP | 0 532 456 A1 | 3/1993 |
| WO | 97/16440 A1 | 5/1997 |
| WO | 01/30348 A1 | 5/2001 |
| WO | 02/32867 A1 | 4/2002 |
| WO | 02/062784 A1 | 8/2002 |

OTHER PUBLICATIONS

Aguiar, M. S. et al., "Effects of microinjections of the neuropeptide substance P in the dorsal periaqueductal gray on the behaviour of rats in the plus-maze test," *Physiol. Behav.*, 1996, 60, 1183-1186.
Antiemetic Subcommittee, "Prevention of chemotherapy- and radiotherapy-induced emesis: results of the Perugia Consensus Conference. Antiemetic Subcommittee of the Multinational Association of Supportive Care in Cancer (MASCC)," *Annals Oncol.*, 1998, 9(8), 811-819.
Arvanitis, L., "Efficacy and Tolerability of Four Novel Compounds in Schizophrenia: Results of the Metatrial Project," *ACNP Meeting*, Dec. 10, 2001, Abstract 144, p. 178.

(Continued)

*Primary Examiner*—Emily Bernhardt
(74) *Attorney, Agent, or Firm*—Woodcock Washburn LLP

(57) ABSTRACT

The invention concerns substituted 1-piperidin-4-yl-4-azetidin-3-yl-piperazine having neurokinin antagonistic activity, in particular $NK_1$ and $NK_1/NK_3$-antagonistic activity, their preparation, compositions comprising them and their use as a medicine, in particular for the treatment of schizophrenia, emesis, anxiety, depression, irritable bowel syndrome (IBS), circadian rhythm disturbances, pain, neurogenic inflammation, asthma, micturition disorders such as urinary incontinence and nociception. The compounds according to the invention can be represented by general Formula (I)

(I)

$$Q\underset{R^2-X}{\overset{}{\diagdown}}N\underset{(CH_2)_n}{\overset{(CH_2)_m}{\diagdown}}\overset{R^1}{\underset{}{\diagdown}}N\underset{(CH_2)_p}{\overset{(R^1)_q}{\diagdown}}N-Alk-Y-Alk-L$$

and comprises also the pharmaceutically acceptable acid or base addition salts thereof, the stereochemically isomeric forms thereof, the N-oxide form thereof and prodrugs thereof, wherein all substituents are defined as in Claim 1.

In view of their capability to antagonize the actions of tachykinins by blocking the neurokinin receptors, and in particular antagonizing the actions of substance P by blocking the NK receptors, the compounds according to the invention are useful as a medicine, in particular in the prophylactic and therapeutic treatment of tachykinin-mediated conditions, such as, for instance CNS disorders, in particular depression, anxiety disorders, stress-related disorders, sleep disorders, cognitive disorders, personality disorders, schizoaffective disorders, eating disorders, neurodegenerative diseases, addiction disorders, mood disorders, sexual dysfunction, pain and other CNS-related conditions; inflammation; allergic disorders; emesis; gastrointestinal disorders, in particular irritable bowel syndrome (IBS); skin disorders; vasospastic diseases; fibrosing and collagen diseases; disorders related to immune enhancement or suppression and rheumatic diseases and body weight control.

13 Claims, No Drawings

OTHER PUBLICATIONS

Ballard, T. M. et al., "Inhibition of shock-induced foot tapping behaviour in the gerbil by a tachykinin NK$_1$ receptor antagonist," *Eur. J. Pharmacol.*, Feb. 2001, 412(3), 255-264.

Bertand, C. et al., "Tachykinin and kinin receptor antagonists: therapeutic perspectives in allergic airway disease," *Trends Pharmacol. Sci.*, 1996, 17(7), 255-259.

Brodin, E. et al., "Effects of sequential removal of rats from a group cage, and of individual housing of rats, on substance P, cholecystokinin and somatostatin levels in the periaqueductal grey and limbic regions," *Neuropeptides*, Apr. 1994, 26(4), 253-260.

Campos et al., "Prevention of cisplatin-induced emesis by the oral neurokinin-1 antagonist, MK-869, in combination with granisetron and dexamethasone or with dexamethasone alone," *J. Clin. Oncol.*, 2001, 19, 1759-1767.

Cocquyt, V. et al., "Comparison of L-758,298, a prodrug for the selective neurokinin-1 antagonist, L-754,030, with ondansetron for the prevention of cisplatin-induced emesis," *Eur. J. Cancer*, May 2001, 37(7), 835-842.

Culman, J. et al., "Central tachykinins: mediators of defence reaction and stress reactions," *Can. J. Physiol. Pharmacol.*, 1995, 73(7), 885-891.

DeMulder et al., "Ondansetron compared with high-dose metoclopramide in prophylaxis of acute and delayed cisplatin-induced nausea and vomiting. A multicenter, randomized, double-blind, crossover study," *Annals of Internal Medicine*, 1990, 113, 834-840.

Elliott, P.J., "Place aversion induced by the substance P analogue, dimethyl-C7, is not state dependent: implication of substance P in aversion," *Exp. Brain Res.* 1988, 73(2), 354-356.

Giardina, G. et al., "Recent Advances in neurokinin-3 receptor antagonists," *Exp. Opin. Ther. Patents*, 2000, 10(6), 939-960.

Hesketh et al., "Proposal for classifying the acute emetogenicity of cancer chemotherapy," *J. Clin. Oncol.*, 1997, 15(1), 103-109.

Hesketh et al., "Randomized phase II study of the neurokinin 1 receptor antagonist CJ-11,974 in the control of cisplatin-induced emesis," *J. Clin. Oncol.*, 1999, 17, 338-343.

Kramer, M. S. et al., "Distinct mechanism for antidepressant activity by blockade of central substance P receptors," *Science*, 1998, 281(5383), 1640-1645.

Krase et al., "Substance P is involved in the sensitization of the acoustic startle response by footshocks in rats," *Behav. Brain. Res.*, 1994, 63, 81-88.

Kris et al., "Incidence, course, and severity of delayed nausea and vomiting following the administration of high-dose cisplatin," *J. Clin. Oncol.*, 1985, 3, 1379-1384.

Lejeune, F. et al., "Selective, non-peptidergic Neurokinin$_1$ (NIK$_1$) Antagonists Enhance the Activity of Frontocortical Dopaminergic and Adrenergic , but not Serotonergic, Pathways in Rats," *Abstracts Soc. Neurosci.*, Abstract No. 477.1, Nov. 2001, p. 1253.

Longmore, J. et al., "Neurokinin Receptors," *DN&P*, 1995, 8(1), 5-23.

Lundberg, J. M., "Tachykinins, sensory nerves, and asthma—an overview," *Can. J. Physiol. Pharmacol.*, 1995, 73(7), 908-914.

Maggi, C. A. et al., "The dual nature of the tachykinin NK$_1$ receptor," *Trends Pharmacol. Sci.*,1997, 18(10), 351-355.

Maggi, C. A., "The mammalian tachykinin receptors," *Gen. Pharmacol.*, 1995, 26(5), 911-944.

Mattson, R. J. et al., "An Improved Method for Reductive Alkylation of Amines Using Titanium (IV) Isopropoxide and Sodium Cyanoborohydride," *J. Org. Chem.*, 1990, 55, 2552-2554.

Megens, A. A. et al., "Pharmacological profil of (2R-trans)-4-[1-[3,5-bis(trifluoromethyl)benzoyl]-2-(phenylmethyl)-4-piperidinyl]-N-(2,6-dimethylphenyl)-1-acetamide (S)-Hydroxybutanedioate (R116301), an orally and centrally active neurokinin-1 receptor antagonist," *J. Pharmacol. Exp. Ther.*, 2002, 302(2), 696-709.

Navari, R. M. et al., "Reduction of cisplatin-induced emesis by a selective neurokinin-1-receptor antagonist. L-754,030 Antiemetic Trials Group," *N. Engl. J. Med.*, 1999, 340(3), 190-195.

Naylor, R. J. et al., "Emesis and anti-emesis," *Cancer Surv.*, 1994, 21, 117-135.

Okano, S. et al., "Effects of TAK-637, a novel neurokinin-1 receptor antagonist, on colonic function in vivo," *J. Pharmacol. Exp. Ther.*, 2001, 298(2), 559-564.

Piedimonte, G. et al., "A new NK$_1$ receptor antagonist (CP-99,994) prevents the increase in tracheal vascular permeability produced by hypertonic saline," *J. Pharmacol. Exp. Ther.*, 1993, 266, 270-273.

Regoli, D. et al., "Receptors and antagonists for substance P and related peptides," *Pharmacol. Rev.*, 1994, 46(4), 551-599.

Roila, F. "Ondansetron plus dexamethasone compared to the 'standard' metoclopramide combination," *Oncology*, 1993, 50(3), 163-167.

Rudd, J. A. et al., "Effects of 5-HT$_3$ receptor antagonists on models of acute and delayed emesis induced by cisplatin in the ferret," *Neuropharmacology*, 1994, 33(12), 1607-1608.

Rudd, J. A. et al., "The action of the NK$_1$ tachykinin receptor antagonist, CP 99,994, in antagonizing the acute and delayed emesis induced by cisplatin in the ferret," *Br. J. Pharmacol.*, 1994, 119(5), 931-936.

Rupniak, N. M. et al., "Discovery of the antidepressant and antiemetic efficacy of substance P receptor (NK1) antagonists," *Trends Pharmacol. Sci.*, 1999, 20(12), 485-490.

Sam, T. S. et al., "Action of glucocorticoids to antagonise cisplatin-induced acute and delayed emesis in the ferret," *Eur. J. Pharmacol.*, 2001, 417(3), 231-237.

Shirayama, Y. et al., "Reduction of substance P after chronic antidepressants treatment in the striatum, substantia nigra and amygdala of the rat," *Brain Res.*, 1996, 739(1-2), 70-78.

Stella, V. J. et al., "Prodrugs. Do they have advantages in clinical practice?" *Drugs*, 1985, 29, 455-473.

Stella, V. J. et al., "Prodrugs", *Drug Delivery Systems*, 1985, pp. 112-176.

Tattersall, F. D. et al., "Tachykinin NK$_1$ receptor antagonists act centrally to inhibit emesis induced by the chemotherapeutic agent cisplatin in ferrets," *Neuropharmacol.*, 1996, 35(8), 1121-1129.

Tattersall, F. D. et al., "The novel NK$_1$ receptor antagonist MK-0869 (L-754,030) and its water soluble phosphoryl prodrug, L-758,298, inhibit acute and delayed cisplatin-induced emesis in ferrets," *Neuropharmacology*, 2000, 39(4), 652-663.

Teixeira, R. M. et al., "Effects of central administration of tachykinin receptor agonists and antagonists on plus-maze behavior in mice," *Eur. J. Pharmacol.*, 1996, 311, 7-14.

Tonini, M. et al., "Tachykinin-dependent and -independent components of peristalsis in the guinea pigs isolated distal colon," *Gastroenterol.*, 2001, 120, 938-945.

Watson, J. W. et al., "The anti-emetic effects of CP-99,994 in the ferret and the dog: role of the NK$_1$ receptor," *Br. J. Pharmacol.*, 1995, 115, 84-94.

Wilson, C. O. et al., (Ed.), *Textbook of Organic Medicinal and Pharmaceutical Chemistry*, Seventh Edition, 1977, J. B. Lippincott Company, pp. 70-75.

SUBSTITUTED 1-PIPERIDIN-4-YL-4-AZETIDIN-3-YL-PIPERAZINE DERIVATIVES AND THEIR USE AS NEUROKININ ANTAGONISTS

CROSS REFERENCE OT RELATED APPLICATIONS

This application is the national stage of Application No. PCT/EP2003/051042, filed 17 Dec. 2003, which application claims priority from PCT/EP2002/14837 filed 23 Dec. 2002, which are hereby incorporated by reference.

FIELD OF THE INVENTION

This invention concerns substituted 1-piperidin-4-yl-4-azetidin-3-yl-piperazine derivatives having neurokinin antagonistic activity, in particular $NK_1$ and $NK_1/NK_3$ antagonistic activity, their preparation, compositions comprising them and their use as a medicine, in particular for the treatment of of schizophrenia, emesis, anxiety, depression, irritable bowel syndrome (IBS), circadian rhythm disturbances, pain, neurogenic inflammation, asthma, micturition disorders such as urinary incontinence and nociception.

BACKGROUND OF THE INVENTION

Tachykinins belong to a family of short peptides that are widely distributed in the mammalian central and peripheral nervous system (Bertrand and Geppetti, *Trends Pharmacol. Sci.* 17:255-259 (1996); Lundberg, *Can. J. Physiol. Pharmacol.* 73:908-914 (1995); Maggi, *Gen. Pharmacol.* 26:911-944 (1995); Regoli et al., *Pharmacol. Rev.* 46 (1994)). They share the common C-terminal sequence Phe-Xaa-Gly-Leu-Met-$NH_2$. Tachykinins released from peripheral sensory nerve endings are believed to be involved in neurogenic inflammation. In the spinal cord/central nervous system, tachykinins may play a role in pain transmission/perception and in some autonomic reflexes and behaviors. The three major tachykinins are Substance P (SP), Neurokinin A (NKA) and Neurokinin B (NKB) with preferential affinity for three distinct receptor subtypes, termed $NK_1$, $NK_2$, and $NK_3$, respectively. However, functional studies on cloned receptors suggest strong functional cross-interaction between the 3 tachykinins and their corresponding receptors (Maggi and Schwartz, *Trends Pharmacol. Sci.* 18: 351-355 (1997)).

Species differences in structure of $NK_1$ receptors are responsible for species-related potency differences of $NK_1$ antagonists (Maggi, *Gen. Pharmacol.* 26:911-944 (1995); Regoli et al., *Pharmacol. Rev.* 46(4):551-599 (1994)). The human $NK_1$ receptor closely resembles the $NK_1$ receptor of guinea-pigs and gerbils but differs markedly from the $NK_1$ receptor of rodents. The development of neurokinin antagonists has led to date to a series of peptide compounds of which might be anticipated that they are metabolically too labile to be employed as pharmaceutically active substances (Longmore J. et al., *DN&P* 8(1):5-23 (1995)).

The tachykinins are involved in schizophrenia, depression, (stress-related) anxiety states, emesis, inflammatory responses, smooth muscle contraction and pain perception. Neurokinin antagonists are in development for indications such as emesis, anxiety and depression, irritable bowel syndrome (IBS), circadian rhythm disturbances, visceral pain, neurogenic inflammation, asthma, micturition disorders, and nociception. In particular, $NK_1$ antagonists have a high therapeutic potential in emesis and depression and $NK_2$ antagonists have a high therapeutic potential in asthma treatments. $NK_3$ antagonists seem to play a role in the treatment of pain/inflammation (Giardina, G. et al. *Exp. Opin. Ther. Patents*, 10(6): 939-960 (2000)) and schizophrenia.

Schizophrenia

The $NK_3$ antagonist SR142801 (Sanofi) was recently shown to have antipsychotic activity in schizophrenic patients without affecting negative symptoms (Arvantis, L. *ACNP Meeting*, December 2001). Activation of $NK_1$ receptors causes anxiety, stressfull events evoke elevated substance P (SP) plasma levels and $NK_1$ antagonists are reported to be anxiolytic in several animal models. The $NK_1$ antagonist from Merck, MK-869 shows antidepressant effects in major depression, but data were not conclusive due to a high placebo response rate. Moreover, the $NK_1$ antagonist from Glaxo-Welcome (S)-GR205,171 was shown to enhance dopamine release in the frontal cortex but not in the striatum (Lejeune et al. *Soc. Neurosci.*, November 2001). It is therefore hypothesized that $NK_3$ antagonism in combination with $NK_1$ antagonism would be beneficial against both positive and negative symptoms of schizophrenia.

Emesis

Nausea and vomiting are among the most distressing side effects of cancer chemotherapy. These reduce the quality of life and may cause patients to delay or refuse, potentially curative drugs (Kris et al., *J. Clin. Oncol.*, 3:1379-1384 (1985)). The incidence, intensity and pattern of emesis is determined by different factors, such as the chemotherapeutic agent, dosage and route of administration. Typically, early or acute emesis starts within the first 4 h after chemotherapy administration, reaching a peak between 4 h and 10 h, and decreases by 12 to 24 h. Delayed emesis (developing after 24 h and continuing until 3-5 days post chemotherapy) is observed with most 'high-emetogenic' chemotherapeutic drugs (level 4 and 5 according to Hesketh et al., *J. Clin. Oncol.* 15:103 (1997)). In humans, these 'high-emetogenic' anti-cancer treatments, including cis-platinum, induce acute emesis in >98% and delayed emesis in 60-90% of cancer patients.

Animal models of chemotherapy such as cisplatin-induced emesis in ferrets (Rudd and Naylor, *Neuropharmacology* 33:1607-1608 (1994); Naylor and Rudd, *Cancer. Surv.* 21:117-135 (1996)) have successfully predicted the clinical efficacy of the 5-$HT_3$ receptor antagonists. Although this discovery has led to a successful therapy for the treatment of chemotherapy- and radiation-induced sickness in cancer patients, 5-$HT_3$ antagonists such as ondansetron and granisetron (either or not associated with dexamethasone) are effective in the control of the acute emetic phase (the first 24 h) but can only reduce the development of delayed emesis (>24 h) with poor efficacy (De Mulder et al., *Annuals of Internal Medicine* 113:834-840 (1990); Roila, *Oncology* 50:163-167 (1993)). Despite these currently most effective treatments for the prevention of both acute and delayed emesis, still 50% of patients suffer from delayed vomiting and/or nausea (Antiemetic Subcommittee, *Annals Oncol.* 9:811-819 (1998)).

In contrast to 5-$HT_3$ antagonists, $NK_1$ antagonists such as CP-99,994 (Piedimonte et al., *L. Pharmacol. Exp. Ther.* 266: 270-273 (1993)) and aprepitant (also known as MK-869 or L-754,030 ; Kramer et al., *Science* 281:1640-1645 (1998); Rupniak and Kramer, *Trends Pharmacol. Sci.* 20:1-12 (1999)) have now been shown to inhibit not only the acute but also the delayed phase of cisplatin-induced emesis in animals (Rudd et al., *Br. J. Pharmacol.* 119:931-936 (1996); Tattersall et al., *Neuropharmacology* 39:652-663 (2000)). $NK_1$ antagonists have also been demonstrated to reduce 'delayed' emesis in man in the absence of concomitant therapy (Cocquyt et al., *Eur. J. Cancer* 37:835-842 (2001); Navari et al., *N. Engl. L.*

Med. 340:190-195 (1999)). When administered together with dexamethasone and 5-HT$_3$ antagonists, moreover, NK$_1$ antagonists (such as MK-869 and CJ-11,974, also known as Ezlopitant) have been shown to produce additional effects in the prevention of acute emesis (Campos et al., *J. Clin. Oncol.* 19:1759-1767 (2001); Hesketh et al., *Clin. Oncol.* 17:338-343 (1999)).

Central tachykinin NK$_1$ receptors play a major role in the regulation of emesis. NK$_1$ antagonists are active against a wide variety of emetic stimuli (Watson et al., *Br. J. Pharmacol.* 115:84-94 (1995); Tattersall et al., *Neuropharmacol.* 35:1121-1129 (1996); Megens et al., *J. Pharmacol. Exp. Ther.* 302:696-709 (2002)). The compounds are suggested to act by blocking central NK$_1$-receptors in the nucleus tractus solitarius. Apart from NK$_1$ antagonism, CNS penetration is thus a prerequisite for the antiemetic activity of these compounds. Loperamide-induced emesis in ferrets can be used as a fast and reliable screening model for the antiemetic activity of NK$_1$ antagonists. Further evaluation of their therapeutic value in the treatment of both the acute and the delayed phases of cisplatin-induced emesis has been demonstrated in the established ferret model (Rudd et al., *Br. J. Pharmacol.* 119: 931-936 (1994)). This model studies both 'acute' and 'delayed' emesis after cisplatin and has been validated in terms of its sensitivity to 5-HT$_3$ receptor antagonists, glucocorticoids (Sam et al., *Eur. J. Pharmacol.* 417:231-237 (2001)) and other pharmacological challenges. It is unlikely that any future anti-emetic would find clinical acceptance unless successfully treating both the 'acute' and 'delayed' phases of emesis.

Anxiety and Depression

Depression is one of the most common affective disorders of modem society with a high and still increasing prevalence, particularly in the younger members of the population. The life time prevalence rates of Major depression (MDD, DSM-IV) is currently estimated to be 10-25% for women and 5-12% for men, whereby in about 25% of patients the life time MDD is recurrent, without full inter-episode recovery and superimposed on dysthymic disorder. There is a high co-morbidity of depression with other mental disorders and, particularly in younger population high association with drug and alcohol abuse. In the view of the fact that depression primarily affects the population between 18-44 years of age e.g. the most productive population, it is obvious that it imposes a high burden on individuals, families and the whole society.

Among all therapeutic possibilities, the therapy with antidepressants is incontestably the most effective. A large number of antidepressants have been developed and introduced to the market in the course of the last 40 years. Nevertheless, none of the current antidepressants fulfill all criteria of an ideal drug (high therapeutic and prophylactic efficacy, rapid onset of action, completely satisfactory short- and long-term safety, simple and favourable pharmacokinetics) or is without side effects which in one or the other way limits their use in all groups and subgroups of depressed patients.

Since no treatment of the cause of depression exists at present, nor appears imminent, and no antidepressant is effective in more than 60-70% of patients; the development of a new antidepressant which may circumvent any of the disadvantages of the available drugs is justified.

Several findings indicate involvement of SP in stress-related anxiety states. Central injection of SP induces a cardiovascular response resembling the classical "fight or flight" reaction characterised physiologically by vascular dilatation in skeletal muscles and decrease of mesenteric and renal blood flow. This cardiovascular reaction is accompanied by a behavioural response observed in rodents after noxious stimuli or stress (Culman and Unger, *Can. J. Physiol. Pharmacol.* 73:885-891 (1995)). In mice, centrally administered NK$_1$ agonists and antagonists are anxiogenic and anxiolytic, respectively (Teixeira et al., *Eur. J. Pharmacol.* 311:7-14 (1996)). The ability of NK$_1$ antagonists to inhibit thumping induced by SP (or by electric shock; Ballard et al., *Trends Pharmacol. Sci.* 17:255-259 (2001)) might correspond to this antidepressant/anxiolytic activity, since in gerbils thumping plays a role as an alerting or warning signal to conspecifics.

The NK$_1$ receptor is widely distributed throughout the limbic system and fear-processing pathways of the brain, including the amygdala, hippocampus, septum, hypothalamus, and periaqueductal grey. Additionally, substance P is released centrally in response to traumatic or noxious stimuli and substance P-associated neurotransmission may contribute to or be involved in anxiety, fear, and the emotional disturbances that accompany affective disorders such as depression and anxiety. In support of this view, changes in substance P content in discrete brain regions can be observed in response to stressful stimuli (Brodin et al., *Neuropeptides* 26:253-260 (1994)).

Central injection of substance P mimetics (agonists) induces a range of defensive behavioural and cardiovascular alterations including conditioned place aversion (Elliott, *Exp. Brain. Res.* 73:354-356 (1988)), potentiated acoustic startle response (Krase et al., *Behav. Brain. Res.* 63:81-88 (1994)), distress vocalisations, escape behaviour (Kramer et al., *Science* 281:1640-1645 (1998)) and anxiety on the elevated plus maze (Aguiar and Brandao, *Physiol. Behav.* 60:1183-1186 (1996)). These compounds did not modify motor performance and co-ordination on the rotarod apparatus or ambulation in an activity cage. Down-regulation of substance P biosynthesis occurs in response to the administration of known anxiolytic and antidepressant drugs (Brodin et al., *Neuropeptides* 26:253-260 (1994); Shirayama et al., *Brain. Res.* 739:70-78 (1996)). Similarly, a centrally administered NK$_1$ agonist-induced vocalisation response in guinea-pigs can be antagonised by antidepressants such as imipramine and fluoxetine as well as L-733,060, an NK$_1$ antagonist. These studies provide evidence suggesting that blockade of central NK$_1$ receptors may inhibit psychological stress in a manner resembling antidepressants and anxiolytics (Rupniak and Kramer, *Trends Pharmacol. Sci.* 20:1-12 (1999)), but without the side effects of present medications.

Irritable Bowel Syndrome (IBS)

Patients with irritable bowel syndrome (IBS) experience impaired quality of life, and utilise health care resources extensively as they seek better "solutions" (including unnecessary repeated investigations or even surgery). Although these patients suffer from a 'benign' disorder (in other words, they will never die or develop significant complications), they nevertheless cause a significant economic burden by extensive health care resource utilisation, and absence from work.

A reasonable number of pre-clinical publications over the role of NK$_1$ receptors in visceral pain has been published. Using NK$_1$ receptor knockout mice and NK$_1$ antagonists in animal models, different groups have demonstrated the important role played by the NK$_1$ receptor in hyperalgesia and visceral pain. The distribution of NK$_1$ receptors and substance P favours a major role in visceral rather than in somatic pain. Indeed more than 80% of visceral primary afferent contain substance P compared with only 25% skin afferents. NK$_1$ receptors are also involved in gastrointestinal motility (Tonini et al., *Gastroenterol.* 120:938-945 (2001); Okano et al., *J. Pharmacol. Exp. Ther.* 298:559-564 (2001)). Because of this dual role in both gastrointestinal motility and in nociception, $NK_1$ antagonists are considered to have potential to ameliorate symptoms in IBS patients.

Background Prior Art

Compounds containing the 1-piperidin-4-yl-piperazinyl moiety were published in WO 97/16440-A1, published May 9, 1997 by Janssen Pharmaceutica N.V. for use as substance P antagonists, in WO 02/32867, published Apr. 25, 2002 by Glaxo Group Ltd. for their special advantages as neurokinin antagonists (more specifically were disclosed 4-piperazin-1-yl-piperidine-1-carboxylic acid amide derivatives), in WO 01/30348-A1, published May 03, 2001 by Janssen Pharmaceutica N.V., for use as substance P antagonists for influencing the circadian timing system, and in WO 02/062784-A1, published Aug. 15, 2002 by Hoffmann-La Roche AG for use as neurokinin-1 antagonists.

The compounds of the present invention differ from the compounds of the prior art in the substitution of the piperazinyl moiety, being a substituted azetidine moiety as well as in their improved ability as potent, orally and centrally active neurokinin antagonists with therapeutic value, especially for the treatment of emesis, anxiety and depression, irritable bowel syndrome (IBS), circadian rhythm disturbances, visceral pain, neurogenic inflammation, asthma, micturition disorders such as urinary incontinence and nociception.

DESCRIPTION OF THE INVENTION

The present invention relates to novel substituted 1-piperidin-4-yl-4-azetidin-3-yl-piperazine derivatives according to the general Formula (I)

the pharmaceutically acceptable acid or base addition salts thereof, the stereochemically isomeric forms thereof, the N-oxide form thereof and prodrugs thereof, wherein:

n is an integer, equal to 0, 1 or 2;
m is an integer, equal to 1 or 2, provided that if m is 2, then n is 1;
p is an integer equal to 1 or 2;
q is an integer equal to 0 or 1;
Q is O or $NR^3$;
X is a covalent bond or a bivalent radical of formula —O—, —S— or —$NR^3$;
each $R^3$ independently from each other, is hydrogen or alkyl;
each $R^1$ independently from each other, is selected from the group of $Ar^1$, $Ar^1$-alkyl and di($Ar^1$)-alkyl;
$R^2$ is $Ar^2$, $Ar^2$-alkyl, di($Ar^2$)alkyl, $Het^1$ or $Het^1$-alkyl
Y is a covalent bond or a bivalent radical of formula —C(=O)—, —$SO_2$—, >C=CH—R or >C=N—R, wherein R is CN or nitro;
each Alk represents, independently from each other, a covalent bond; a bivalent straight or branched, saturated or unsaturated hydrocarbon radical having from 1 to 6 carbon atoms ; or a cyclic saturated or unsaturated hydrocarbon radical having from 3 to 6 carbon atoms ; each radical optionally substituted on one or more carbon atoms with one or more alkyl, phenyl, halo, cyano, hydroxy, formyl and amino radicals;

L is selected from the group of hydrogen, alkyl, alkyloxy, $Ar^3$-oxy, alkyloxycarbonyl, alkylcarbonyloxy, mono- and di(alkyl)amino, mono-and di($Ar^3$)amino, mono-and di(alkyloxycarbonyl)amino, $Ar^3$, $Ar^3$carbonyl, $Het^2$ and $Het^2$carbonyl;

$Ar^1$ is phenyl, optionally substituted with 1, 2 or 3 substituents, each independently from each other, selected from the group of halo, alkyl, cyano, aminocarbonyl and alkyloxy;

$Ar^2$ is naphtalenyl or phenyl, each optionally substituted with 1, 2 or 3 substituents, each independently from each other, selected from the group of halo, nitro, amino, mono- and di(alkyl)amino, cyano, alkyl, hydroxy, alkyloxy, carboxyl, alkyloxycarbonyl, aminocarbonyl and mono- and di(alkyl) aminocarbonyl;

$Ar^3$ is naphthalenyl or phenyl, optionally substituted with 1, 2 or 3 substituents, each independently from each other, selected from the group of alkyloxy, alkyl, halo, hydroxy, pyridinyl, morpholinyl, pyrrolidinyl, imidazo[1,2-α]pyridinyl, morpholinylcarbonyl, pyrrolidinylcarbonyl, amino and cyano;

$Het^1$ is a monocyclic heterocyclic radical selected from the the group of pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl and benzothienyl; each heterocyclic radical may optionally be substituted on any atom by a radical selected from the group of halo and alkyl;

$Het^2$ is a monocyclic heterocyclic radical selected from the group of pyrrolidinyl, dioxolyl, imidazolidinyl, pyrrazolidinyl, piperidinyl, morpholinyl, dithianyl, thiomorpholinyl, piperazinyl, imidazolidinyl, tetrahydrofuranyl, 2H-pyrrolyl, pyrrolinyl, imidazolinyl, pyrrazolinyl, pyrrolyl, imidazolyl, pyrazolyl, triazolyl, furanyl, thienyl, oxazolyl, isoxazolyl, thiazolyl, thiadiazolyl, isothiazolyl, pyridinyl, pyrimidinyl, pyrazinyl, pyridazinyl and triazinyl;

or a bicyclic heterocyclic radical selected from the group of benzopiperidinyl, quinolinyl, quinoxalinyl, indolyl, isoindolyl, chromenyl, benzimidazolyl, imidazo[1,2-α]pyridinyl, benzoxazolyl, benzisoxazolyl, benzothiazolyl, benzisothiazolyl, benzofuranyl and benzothienyl;

each radical optionally substituted with one or more radicals selected from the group of $Ar^1$, $Ar^1$alkyl, halo, hydroxy, alkyl, piperidinyl, pyrrolyl, thienyl, oxo, alkyloxy, alkyloxyalkyl and alkyloxycarbonyl; and alkyl is a straight or branched saturated hydrocarbon radical having from 1 to 6 carbon atoms or a cyclic saturated hydrocarbon radicals having from 3 to 6 carbon atoms; optionally substituted on one or more carbon atoms with one or more radicals selected from the group of phenyl, halo, cyano, oxo, hydroxy, formyl and amino.

More in particular, the invention relates to a compound according to the general Formula (I), the pharmaceutically acceptable acid or base addition salts thereof, the stereochemically isomeric forms thereof, the N-oxide form thereof and a prodrug thereof, wherein:

n is 1;
m is 1;
p is 1;
q is 0;
Q is O;

X is a covalent bond;
each $R^1$ is $Ar^1$ or $Ar^1$-alkyl;
$R^2$ is $Ar^2$;
Y is a covalent bond or a bivalent radical of formula —C(=O)— or —SO$_2$—;
each Alk represents, independently from each other, a covalent bond; a bivalent straight saturated hydrocarbon radical having from 1 to 6 carbon atoms; each radical optionally substituted on one or more carbon atoms with one or more phenyl radicals;
L is selected from the group of hydrogen, alkyl, mono-and di(alkyloxycarbonyl)amino, $Ar^3$ and $Het^2$;
$Ar^1$ is phenyl;
$Ar^2$ is phenyl, each optionally substituted with 1,2 or 3 alkyl substituents;
$Ar^3$ is phenyl, optionally substituted with 1 or 2 substituents, each independently from each other selected from the group of halo and cyano;
$Het^2$ is a monocyclic heterocyclic radical selected from the group of tetrahydrofuranyl, pyrrolidinyl, pyrazolyl, furanyl, thienyl, pyrimidinyl, thiadiazolyl and pyridinyl ; each radical optionally substituted with one or more alkyl or alkyloxycarbonyl radicals; and
alkyl is a straight saturated hydrocarbon radical having from 1 to 6 carbon atoms or a cyclic saturated hydrocarbon radicals having from 3 to 6 carbon atoms.

More in particular, the invention relates to a compound according to the general Formula (I), the pharmaceutically acceptable acid or base addition salts thereof, the stereochemically isomeric forms thereof, the N-oxide form thereof and a prodrug thereof, wherein $R^1$ is $Ar^1$methyl and attached to the 2-position or $R^1$ is $Ar^1$ and attached to the 3-position, as exemplified in either of the following formulas for compounds according to Formula (I) wherein m and n are equal to 1 and Ar is an unsubstituted phenyl.

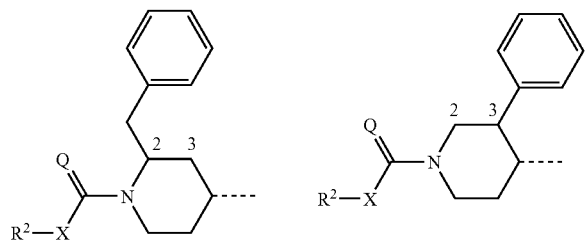

More in particular, the invention relates to a compound according to the general Formula (I), the pharmaceutically acceptable acid or base addition salts thereof, the stereochemically isomeric forms thereof, the N-oxide form thereof and a prodrug thereof, wherein the $R^2$—X—C(=Q)— moiety is 3,5-di-(trifluoromethyl) phenylcarbonyl.

More in particular, the invention relates to a compound according to the general Formula (I), the pharmaceutically acceptable acid or base addition salts thereof, the stereochemically isomeric forms thereof, the N-oxide form thereof and a prodrug thereof, wherein p is 1.

More in particular, the invention relates to a compound according to the general Formula (I), the pharmaceutically acceptable acid or base addition salts thereof, the stereochemically isomeric forms thereof, the N-oxide form thereof and a prodrug thereof, wherein Y is —C(=O)—.

More in particular, the invention relates to a compound according to the general Formula (I), the pharmaceutically acceptable acid or base addition salts thereof, the stereochemically isomeric forms thereof, the N-oxide form thereof and a prodrug thereof, wherein Alk is a covalent bond.

More in particular, the invention relates to a compound according to the general Formula (I), the pharmaceutically acceptable acid or base addition salts thereof, the stereochemically isomeric forms thereof, the N-oxide form thereof and a prodrug thereof, wherein L is $Het^2$.

More in particular, the invention relates to a compound according to the general Formula (I), the pharmaceutically acceptable acid or base addition salts thereof, the stereochemically isomeric forms thereof, the N-oxide form thereof and a prodrug thereof, wherein the compound is a compound selected from the group of compounds with compound number 2, 3, 4, 5, 6, 7, 8, 9, 10, 11, 12, 13, 14, 15, 16, 17, 18, 19, 20, 21 and 22 as mentioned in Table 1 further in this application.

In the framework of this application, alkyl is defined as a monovalent straight or branched saturated hydrocarbon radical having from 1 to 6 carbon atoms, for example methyl, ethyl, propyl, butyl, 1-methylpropyl, 1,1-dimethylethyl, pentyl, hexyl; alkyl further defines a monovalent cyclic saturated hydrocarbon radical having from 3 to 6 carbon atoms, for example cyclopropyl, methylcyclopropyl, cyclobutyl, cyclopentyl and cyclohexyl. The definition of alkyl also comprises an alkyl radical that is optionally substituted on one or more carbon atoms with one or more phenyl, halo, cyano, oxo, hydroxy, formyl and amino radicals, for example hydroxyalkyl, in particular hydroxymethyl and hydroxyethyl and polyhaloalkyl, in particular difluoromethyl and trifluoromethyl.

In the framework of this application, halo is generic to fluoro, chloro, bromo and iodo.

In the framework of this application, with "compounds according to the invention" is meant a compound according to the general Formula (I), the pharmaceutically acceptable acid or base addition salts thereof, the stereochemically isomeric forms thereof, the N-oxide form thereof and a prodrug thereof.

In the framework of this application, especially in the moiety $Alk^a$—Y—$Alk^b$ in Formula (I), when two or more consecutive elements of said moiety denote a covalent bond, then a single covalent bond is denoted. For example, when $Alk^a$ and Y denote both a covalent bond and $Alk^b$ is $CH_2$, then the moiety $Alk^a$—Y—$Alk^b$ denotes —$CH_2$. Similary, if $Alk^a$, Y and $Alk^b$ each denote a covalent bond and L denotes H, then the moiety $Alk^a$—Y—$Alk^b$ denotes —H.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate base or acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more tertiary nitrogens (e.g of the piperazinyl or azetidyl radical) are N-oxidized. Such N-oxides can easily be obtained by a skilled person without any inventive skills and they are obvious alternatives for the compounds according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

The compounds according to the invention possess at least 2 oxydizable nitrogens (tertiary amines moieties). It is therefore highly likely that N-oxides are to form in the human metabolism.

The compounds of Formula (I) may be converted to the corresponding N-oxide forms following art-known procedures for converting a trivalent nitrogen into its N-oxide form. Said N-oxidation reaction may generally be carried out by reacting the starting material of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. R* and S* each indicate optically pure stereogenic centers with undetermined absolute configuration. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

Compounds according to Formula (I) and some of the intermediate compounds have at least two stereogenic centers in their structure.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 112-176, and *Drugs*, 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$alkyl, phenyl, benzyl or one of the following groups:

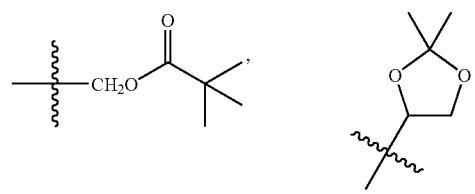

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl. Compounds according to the invention having an amino group may be derivatised with a ketone or an aldehyde such as formaldehyde to form a Mannich base. This base will hydrolyze with first order kinetics in aqueous solution.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

Substance P and other neurokinins are involved in a variety of biological actions such as pain transmission (nociception), neurogenic inflammation, smooth muscle contraction, plasma protein extravasation, vasodilation, secretion, mast cell degranulation, and also in activation of the immune system. A number of diseases are deemed to be engendered by activation of neurokinin receptors, in particular the $NK_1$ receptor, by excessive release of substance P and other neurokinins in particular cells such as cells in the neuronal plexi of the gastrointestinal tract, unmyelinated primary sensory afferent neurons, sympathetic and parasympathetic neurons and nonneuronal cell types (DN&P 8(1):5-23 (1995) and Longmore J. et al., "Neurokinin Receptors" *Pharmacological Reviews* 46(4):551-599 (1994)).

The compounds of the present invention are potent inhibitors of neurokinin-mediated effects, in particular those mediated via the $NK_1$ receptor and the $NK_1/NK_3$ receptors, and may therefore be described as neurokinin antagonists, especially as substance P antagonists, as may be indicated in vitro by the antagonism of substance P-induced relaxation of pig coronary arteries. The binding affinity of the present compounds for the human, guinea-pig and gerbil neurokinin receptors may also be determined in vitro in a receptor binding test using $^3$H-substance-P as radioligand. The subject compounds also show substance-P antagonistic activity in vivo as may be evidenced by, for instance, the antagonism of substance P-induced plasma extravasation in guinea-pigs, or the antagonism of drug-induced emesis in ferrets (Watson et al., *Br. J. Pharmacol.* 115:84-94 (1995)).

In view of their capability to antagonize the actions of neurokinins by blocking the neurokinin receptors, and in particular by blocking the $NK^1$, $NK^2$ and $NK^3$ receptor, the compounds according to the invention are useful as a medicine, in particular in the prophylactic and therapeutic treatment of tachykinin-mediated conditions.

More in particular, it has been found that some compounds exhibit $NK_1$ antagonistic activity or a combined $NK_1/NK_3$ antagonistic activity as can be seen from the Table 4 in the experimental section.

The invention therefore relates to a compound according to the general Formula (I), the pharmaceutically acceptable acid or base addition salts thereof, the stereochemically isomeric forms thereof, the N-oxide form thereof and prodrugs thereof, for use as a medicine.

The invention also relates to the use of a compound according to the invention for the manufacture of a medicament for treating, either prophylactic or therapeutic or both, tachykinin mediated conditions.

The compounds according to the invention are useful in the treatment of CNS disorders, in particular depression, anxiety disorders, stress-related disorders, sleep disorders, cognitive disorders, personality disorders, schizoaffective disorders, eating disorders, neurodegenerative diseases, addiction disorders, mood disorders, sexual dysfunction, pain and other CNS-related conditions; inflammation; allergic disorders; emesis; gastrointestinal disorders, in particular irritable bowel syndrome (IBS); skin disorders; vasospastic diseases; fibrosing and collagen diseases; disorders related to immune enhancement or suppression and rheumatic diseases and body weight control.

In particular, the compounds according to the invention are useful in the treatment or prevention of depression including but not limited to major depressive disorders including bipolar depression; unipolar depression; single or recurrent major depressive episodes with or without psychotic features, catatonic features, melancholic features, atypical features or postpartum onset, and, in the case of recurrent episodes, with or without seasonal pattern. Other mood disorders encompassed within the term "major depressive disorder" include dysthymic disorder with early or late onset and with or without atypical features, bipolar I disorder, bipolar II disorder, cyclothymic disorder, recurrent brief depressive disorder, mixed affective disorder, neurotic depression, post traumatic stress disorder and social phobia; dementia of the Alzheimer's type with early or late onset, with depressed mood; vascular dementia with depressed mood; substance-induced mood disorders such as mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

In particular, the compounds according to the invention are useful in the treatment or prevention of anxiety disorders, including but not limited to panic attack; agoraphobia; panic disorder without agoraphobia; agoraphobia without history of panic disorder; specific phobia; social phobia; obsessive-compulsive disorder; post-traumatic stress disorder; acute stress disorder; generalized anxiety disorder; anxiety disorder due to a general medical condition; substance-induced anxiety disorder; and anxiety disorder not otherwise specified.

In particular, the compounds according to the invention are useful in the treatment or prevention of stress-related disorders associated with depression and/or anxiety, including but not limited to acute stress reaction; adjustment disorders, such as brief depressive reaction, prolonged depressive reaction, mixed anxiety and depressive reaction, adjustment disorder with predominant disturbance of other emotions, adjustment disorder with predominant disturbance of conduct, adjustment disorder with mixed disturbance of emotions and conduct and adjustment disorders with other specified predominant symptoms; and other reactions to severe stress.

In particular, the compounds according to the invention are useful in the treatment or prevention of sleep disorders, including but not limited to dysomnia and/or parasomnias as primary sleep disorders; insomnia; sleep apnea; narcolepsy; circadian rhythms disorders; sleep disorders related to another mental disorder; sleep disorder due to a general medical condition; and substance-induced sleep disorder.

In particular, the compounds according to the invention are useful in the treatment or prevention of cognitive disorders, including but not limited to dementia; amnesic disorders and cognitive disorders not otherwise specified, especially dementia caused by degenerative disorders, lesions, trauma, infections, vascular disorders, toxins, anoxia, vitamin deficiency or endocrinic disorders; dementia of the Alzheimer's type, with early or late onset, with depressed mood; AIDS-associated dementia or amnesic disorders caused by alcohol or other causes of thiamin deficiency, bilateral temporal lobe damage due to Herpes simplex encephalitis and other limbic encephalitis, neuronal loss secondary to anoxia/hypoglycemia/severe convulsions and surgery, degenerative disorders, vascular disorders or pathology around ventricle III. Furthermore, the compounds according to the invention are also useful as memory and/or cognition enhancers in healthy humans with no cognitive and/or memory deficit.

In particular, the compounds according to the invention are useful in the treatment or prevention of personality disorders, including but not limited to paranoid personality disorder; schizoid personality disorder; schizotypical personality disorder; antisocial personality disorder; borderline personality disorder; histrionic personality disorder; narcissistic personality disorder; avoidant personality disorder; dependent personality disorder; obsessive-compulsive personality disorder and personality disorder not otherwise specified.

In particular, the compounds according to the invention are useful in the treatment or prevention of schizoaffective disorders resulting from various causes, including schizoaffective disorders of the manic type, of the depressive type, of mixed type; paranoid, disorganized, catatonic, undifferentiated and residual schizophrenia; schizophreniform disorder; delusional disorder; brief psychotic disorder; shared psychotic disorder; substance-induced psychotic disorder; and psychotic disorder not otherwise specified.

In particular, the compounds according to the invention are also useful in the treatment or prevention of eating disorders, including anorexia nervosa; atypical anorexia nervosa; bulimia nervosa; atypical bulimia nervosa; overeating associated with other psychological disturbances; vomiting associated with other psychological disturbances; and non-specified eating disorders.

In particular, the compounds according to the invention are also useful in the treatment or prevention of neurodegenerative diseases, including but not limited to Alzheimer's disease; Huntington's chorea; Creutzfeld-Jacob disease; Pick's disease; demyelinating disorders, such as multiple sclerosis and ALS; other neuropathies and neuralgia; multiple sclerosis; amyotropical lateral sclerosis; stroke and head trauma.

In particular, the compounds according to the invention are also useful in the treatment or prevention of addiction disorders, including but not limited to substance dependence or abuse with or without physiological dependence, particularly where the substance is alcohol, amphetamines, amphetamine-like substances, caffeine, cocaine, hallucinogens, inhalants, nicotine, opioids (such as cannabis, heroin and morphine), phencyclidine, phencyclidine-like compounds, sedative-hypnotics, benzodiazepines and/or other substances, particularly useful for treating withdrawal from the above substances and alcohol withdrawal delirium.

In particular, the compounds according to the invention are also useful in the treatment or prevention of mood disorders induced particularly by alcohol, amphetamines, caffeine, cannabis, cocaine, hallucinogens, inhalants, nicotine, opioids, phencyclidine, sedatives, hypnotics, anxiolytics and other substances.

In particular, the compounds according to the invention are also useful in the treatment or prevention of sexual dysfunction, including but not limited to sexual desire disorders; sexual arousal disorders; orgasmic disorders; sexual pain disorders; sexual dysfunction due to a general medical condition; substance-induced sexual dysfunction and sexual dysfunction not otherwise specified.

In particular, the compounds according to the invention are also useful in the treatment or prevention of pain, including but not limited to traumatic pain such as postoperative pain; traumatic avulsion pain such as brachial plexus; chronic pain such as arthritic pain such as occurring in osteo- rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy and phantom limb pain; various forms of headache such as migraine, acute or chronic tension headache, temporomandibular pain, maxillary sinus pain and cluster headache; odontalgia; cancer pain; visceral pain; gastrointestinal pain; nerve entrapment pain; sport's injury pain; dysmennorrhoea; menstrual pain; meningitis; arachnoiditis; musculoskeletal pain; low back pain such as spinal stenosis, prolapsed disc, sciatica, angina, ankylosing spondyolitis; gout; burns; scar pain; itch; and thalamic pain such as post stroke thalamic pain.

In particular, the compounds according to the invention are also useful in the treatment or prevention of the following other CNS-related conditions: akinesia, akinetic-rigid syndromes, dyskinesia and medication-induced parkinsonism, Gilles de la Tourette syndrome and its symptoms, tremor, chorea, myoclonus, tics and dystonia, attention-deficit/hyperactivity disorder (ADHD), Parkinson's disease, drug-induced Parkinsonism, post-encephalitic Parkinsonism, progressive supranuclear palsy, multiple system atrophy, corticobasal degeneration, parkinsonism-ALS dementia complex and basal ganglia calcification, behavioral disturbances and conduct disorders in dementia and the mentally retarded, including restlessness and agitation, extra-pyramidal movement disorders, Down's syndrome and Akathisia.

In particular, the compounds according to the invention are also useful in the treatment or prevention of inflammation, including but not limited to inflammatory conditions in asthma, influenza, chronic bronchitis and rheumatoid arthritis; inflammatory conditions in the gastrointestinal tract such as, but not limited to Crohn's disease, ulcerative colitis, inflammatory bowel disease and non-steroidal anti-inflammatory drug induced damage; inflammatory conditions of the skin such as herpes and eczema; inflammatory conditions of the bladder such as cystitis and urge incontinence; eye and dental inflammation and pancreatitis, in particular chronic and acute pacreatitis.

In particular, the compounds according to the invention are also useful in the treatment or prevention of allergic disorders, including but not limited to allergic disorders of the skin such as but not limited to urticaria; and allergic disorders of the airways such as but not limited to rhinitis.

In particular, the compounds according to the invention are also useful in the treatment or prevention of emesis, i.e. nausea, retching and vomiting, including but not limited to acute emesis, delayed emesis and anticipatory emesis; emesis induced by drugs such as cancer chemotherapeutic agents such as alkylating agents, for example cyclophosphamide, carmustine, lomustine and chlorambucil; cytotoxic antibiotics, for example dactinomycin, doxorubicin, mitomycin-C and bleomycin; anti-metabolites, for example cytarabine, methotrexate and 5-fluorouracil; vinca alkaloids, for example etoposide, vinblastine and vincristine; and other drugs such as cisplatin, dacarbazine, procarbazine and hydroxyurea; and combinations thereof; radiation sickness; radiation therapy, such as in the treatment of cancer; poisons; toxins such as toxins caused by metabolic disorders or by infection, such as gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, such as myocardial infarction or peritonitis; migraine; increased intracranial pressure; decreased intracranial pressure (such as altitude sickness); opioid analgesics, such as morphine; gastro-oesophageal reflux disease; acid indigestion; over-indulgence of food or drink; acid stomach; sour stomach; waterbrash/regurgitation; heartburn, such as episodic heartburn, nocturnal heartburn and meal induced heartburn; and dyspepsia.

In particular, the compounds according to the invention are also useful in the treatment or prevention of gastrointestinal disorders, including but not limited to irritable bowel syndrome (IBS), skin disorders such as psoriasis, pruritis and sunburn; vasospastic diseases such as angina, vascular headache and Reynaud's disease, cerebral ischaemia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; cough; and body weight control, including obesity.

Most in particular, the compounds according to the invention are useful for the manufacture of a medicament for treating schizophrenia, emesis, anxiety, depression, irritable bowel syndrome (IBS), circadian rhythm disturbances, pain, neurogenic inflammation, asthma, micturition disorders such as urinary incontinence and nociception.

The present invention also relates to a method for the treatment and/or prophylaxis of tachykinin-mediated diseases, in particular for the treatment and/or prophylaxis of schizophrenia, emesis, anxiety, depression, irritable bowel syndrome (IBS), circadian rhythm disturbances, pain, neurogenic inflammation, asthma, micturition disorders such as urinary incontinence and nociception comprising administering to a human in need of such administration an effective amount of a compound according to the invention, in particular according to Formula (I), the pharmaceutically acceptable acid or base addition salts thereof, the stereochemically isomeric forms thereof, the N-oxide form thereof, as well as the pro-drugs thereof.

The invention also relates to a pharmaceutical composition comprising a pharmaceutically acceptable carrier and, as active ingredient, a therapeutically effective amount of a compound according to the invention, in particular a compound according to Formula (I), the pharmaceutically acceptable acid or base addition salts thereof, the stereochemically isomeric forms thereof, the N-oxide form thereof and a pro-drug thereof The compounds according to the invention, in particular the compounds according to Formula (I), the pharmaceutically acceptable acid or base addition salts thereof, the stereochemically isomeric forms thereof, the N-oxide form thereof and the prodrugs thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable $NK_1$ and $NK_1/NK_3$-antagonists, pharmaceutical compositions comprising said compounds for administration orally are especially advantageous.

Synthesis

The compounds according to the invention can generally be prepared by a succession of steps, each of which is known to the skilled person.

The final compounds of Formula (I) are conveniently prepared by alkylating an intermediate compound of Formula (II) with an intermediate compound of Formula (III). Said alkylation may be performed in a reaction-inert solvent such as, for example, 4-methyl-2-pentanone and in the presence of an appropriate salt, such as, for example, sodium carbonate. Stirring and optionally elevated temperatures and/or pressure may enhance the rate of the reaction.

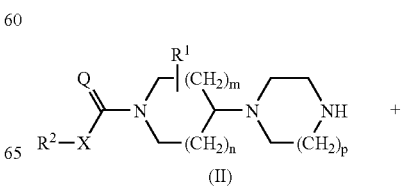
(II)

-continued

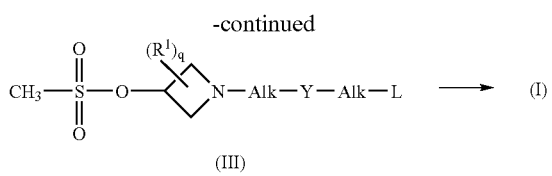

(III)

In this and the following preparations, the reaction products may be isolated from the reaction medium and, if necessary, further purified according to methodologies generally known in the art such as, for example, extraction, crystallization, trituration and chromatography.

Especially advantageous is the preparation of a final compound according to Formula (I) according to the previously mentioned reaction scheme in which the Alk-Y-Alk-L-moiety is diphenylmethyl, thus giving rise to a compound according to Formula (I) in which the Alk-Y-Alk-L-moiety is diphenylmethyl. Said final compound is pharmacologically active and can be converted into a final compound according to the invention in which the Alk-Y-Alk-L-moiety is hydrogen by reductive hydrogenation using e.g. hydrogen as a reducing agent in combination with a suitable catalyst such as, for example, palladium-on-charcoal or platinum-on-charcoal. The resulting final compound according to the invention can then be converted into other compounds according to Formula (I) by art-known transformations, e.g. acylation and alkylation.

In particular, the final compounds of Formula ($I^a$) can be prepared by reacting a final compound of Formula (I') with an intermediate compound of Formula (V) wherein $W^1$ is an appropriate leaving group such as, for example, a halogen, e.g. chloro or bromo, or a sulfonyloxy leaving group, e.g. methanesulfonyloxy or benzenesulfonyloxy. The reaction can be performed in a reaction-inert solvent such as, for example, a chlorinated hydrocarbon, e.g. dichloromethane or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried out at a temperature ranging between room temperature and reflux temperature.

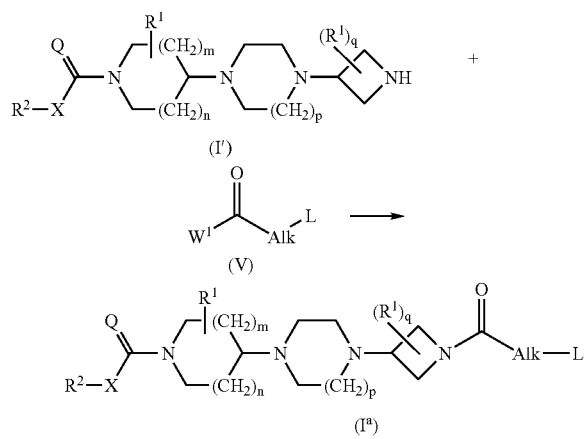

Alternatively, the final compounds of Formula ($I^a$) can also be prepared by reacting a final compound of Formula (I') with a carboxylic acid of Formula (VI). The reaction can be performed in a reaction-inert solvent such as, for example, a chlorinated hydrocarbon, e.g. dichloromethane, in the presence of a suitable base such as, for example, sodium carbonate, sodium hydrogen carbonate or triethylamine and in the presence of an activator, such as e.g. DCC (dicyclohexylcarbodiimide), CDI (carbonyldiimidazole) and EDCI (1-(3-dimethylaminopropyl)-3-ethylcarbodi-imide.HCl). Stirring may enhance the rate of the reaction. The reaction may conveniently be carried out at a temperature ranging between room temperature and reflux temperature.

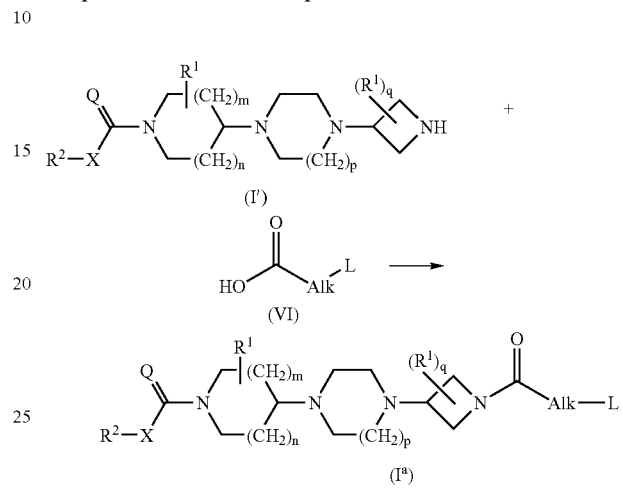

In particular, the final compounds of Formula ($I^b$) can be prepared by reacting a final compound of Formula (I') with a compound of Formula (VII) wherein $W^2$ is an appropriate leaving group such as, for example, a halogen, e.g. chloro or bromo, or a sulfonyloxy leaving group, e.g. methanesulfonyloxy or benzenesulfonyloxy. The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried out at a temperature ranging between room temperature and reflux temperature.

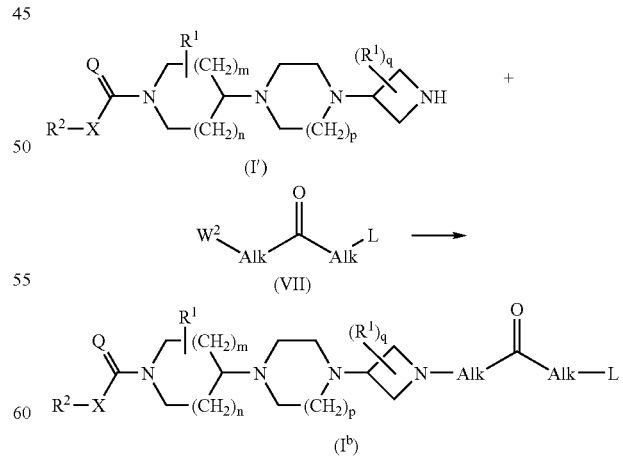

The final compounds of Formula ($I^c$) and Formula ($I^d$) can be prepared either by reductive amination or alkylation of a final compound of Formula (I') with either a compound of Formula (VIII) or (IX) wherein $W^3$ in Formula (VIII) is an appropriate leaving group such as, for example, a halogen, e.g. chloro or bromo, or a sulfonyloxy leaving group, e.g. methanesulfonyloxy or benzenesulfonyloxy and wherein —CH$_2$-Alk in Formula (I$^d$) is -Alk. The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried out at a temperature ranging between room temperature and reflux temperature.

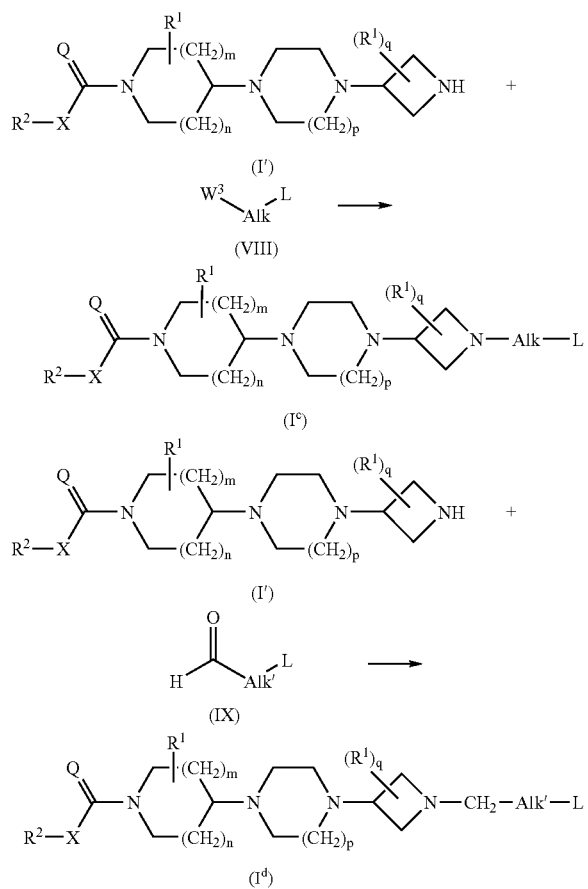

The starting materials and some of the intermediates are known compounds and are commercially available or may be prepared according to conventional reaction procedures generally known in the art. For example, intermediate compounds of Formula (II) may be prepared by reductively N-alkylating an intermediate compound of Formula (XI) with an intermediate compound of Formula (XII) in which W$^4$ is a benzyl radical, after which the resulting compound is subsequently reduced to yield an intermediate compound according to Formula (II). Said reductive N-alkylation may be performed in a reaction-inert solvent such as, for example, dichloromethane, ethanol, toluene or a mixture thereof, and in the presence of an appropriate reducing agent such as, for example, a borohydride, e.g. sodium borohydride, sodium cyanoborohydride or triacetoxy borohydride. In case a borohydride is used as a reducing agent, it may be convenient to use a complex-forming agent such as, for example, titanium (IV)iso-propylate as described in J. Org. Chem, 1990, 55, 2552-2554. Using said complex-forming agent may also result in an improved cis/trans ratio in favour of the trans isomer. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

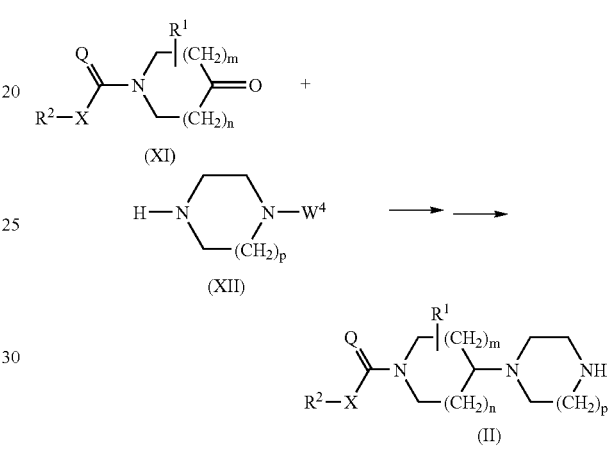

The preparation of intermediate compounds (XI) and (XII) and other intermediates is described in WO 97/16440-A1, published May 9, 1997 by Janssen Pharmaceutica N.V., which is incorporated herein by reference as well as in EP-0, 532,456-A and U.S. Pat. No. 5,310,743. The relevant sections of WO 97/16440-A1 are reproduced below:

The compounds of formula (I) can be prepared by reductively N-alkylating an intermediate of formula (III) with an intermediate of formula (II). Said reductive N-alkylation may be performed in a reaction-inert solvent such as, for example, dichloromethane, ethanol, toluene or a mixture thereof, and in the presence of an appropriate reducing agent such as, for example, a borohydride, e.g. sodium borohydride, sodium cyanoborohydride or triacetoxy borohydride. In case a borohydride is used as a reducing agent, it may be convenient to use a complex-forming agent such as, for example, titanium (IV)isopropylate as described in J. Org. Chem, 1990, 55, 2552-2554. Using said complex-forming agent may also result in an improved cis/trans ratio in favour of the trans isomer. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or qiuinoline-sulphur. Stirring and optionally elevated temperatures and/or pressure may enhance the rate of the reaction.

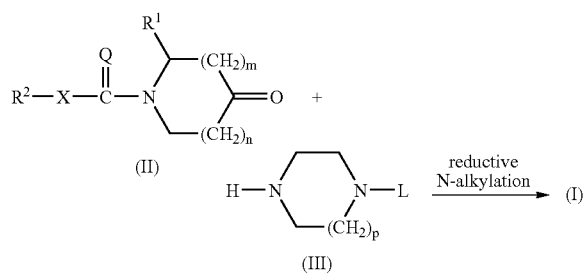

In this and the following preparations, the reaction products may be isolated from the reaction medium and, if necessary, further purified according to methodologies generally known in the art such as, for example, extraction, crystallization, trituration and chromatography.

The compounds of formula (I) can also be prepared by reacting an intermediate of formula (IV) wherein $W^1$ is an appropriate leaving group such as, for example, a halogen, e.g. chloro or bromo, or a sulfonyloxy leaving group, e.g. methanesulfonyloxy or benzenesulfonyloxy, with an intermediate of formula (V). The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried at a temperature ranging between room temperature and reflux temperature.

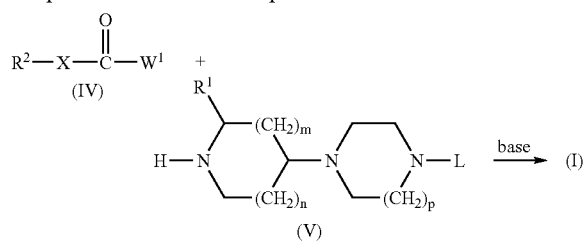

The compounds of formula (I) may also be converted into each other following art-known transformations. In particular, the compounds of formula (I) wherein L is other than hydrogen, said L being represented by L' and said compounds being represented by formula (I-a), can also be prepared by reacting a compound of formula (I) wherein L is hydrogen, said compounds being represented by formula (I-b), with an intermediate of formula (VI) wherein $W^2$ is an appropriate leaving group such as, for example, a halogen, e.g. chloro or bromo, or a sulfonyloxy leaving group, e.g. methanesulfonyloxy or benzenesulfonyloxy, at reaction conditions which are similar to those for the reaction between intermediates of formula (IV) and (V).

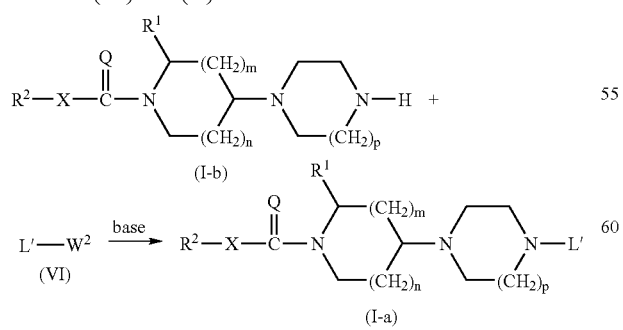

Compounds of formula (I-b) may be prepared by reductively N-alkylating a piperazine derivative of formula (VII) wherein $P^1$ is a protective group such as, for example, benzyl, with an intermediate of formula (II). Said reaction may be performed in a similar way as described hereinabove for the reductive N-alkylation using intermediates (II) and (III). The thus formed compound of formula (I-c) may then be deprotected using art-known deprotection techniques. Depending on the nature of the protective group $P^1$ compounds of formula (I-c) may be part of the scope of the compounds of formula (I).

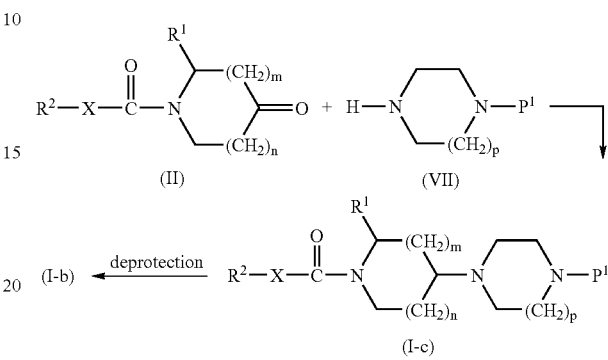

Alternatively, compounds of formula (I-b) may be prepared by first reductively N-alkylating a piperazine derivative of formula (VII) wherein $P^1$ is a protective group such as, for example, halo, with an intermediate of formula (VIII) using the same procedure as described hereinabove for the reductive N-alkylation using intermediates (II) and (III). The thus formed intermediate of formula (XI) may then be reacted with an intermediate of formula (IV) in a reaction-inert solvent and optionally in the presence of a suitable base such as, for example, triethylamine, to form a compound of formula (I-c), which may then be deprotected using art-known deprotection techniques.

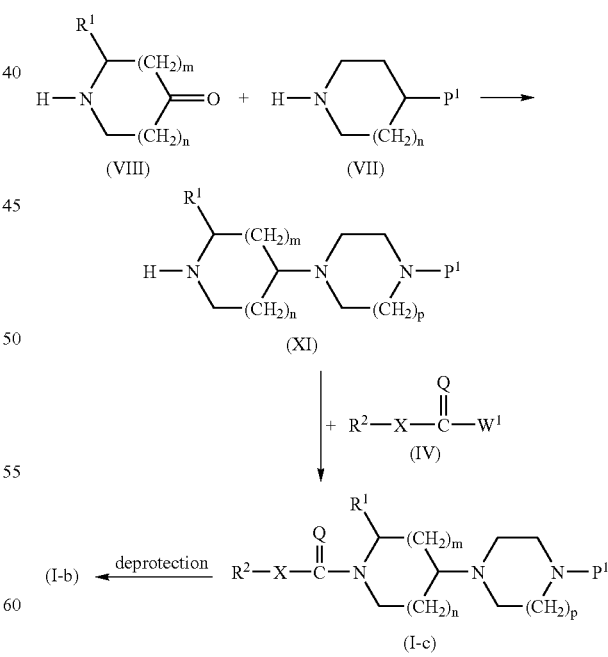

The compounds of formula (I-b) are deemed to be of particular use in the synthesis of other compounds of formula (I).

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide: appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials and some of the intermediates are known compounds and are commercially available or may be prepared according to conventional reaction procedures generally known in the art. For example, intermediates of formula (III), (IV) and (VI) may be prepared according to art-known procedures.

Intermediates of formula (II) may be prepared by condensing an intermediate of formula (IV) with an intermediate of formula (VIII) analogous to the procedure described in EP-0, 532,456-A.

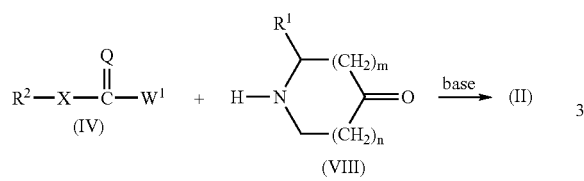

The preparation of intermediates of formula (VIII) is also described in EP-0,532,456-A. However, intermediates of formula (VIII) wherein $R^1$ is optionally substituted $Ar^1C_{1-6}$alkyl or di($Ar^1$)$C_{1-6}$alkyl, said $R^1$ being represented by —CH($R^{1a}$)$_2$ and said intermediates being represented by formula (VIII-a), may also be prepared as depicted in scheme 1.

reduced to an intermediate of formula (IX-d). Said intermediate (IX-d) may in turn be deprotected, thus forming an intermediate of formula (VIII-a). Subsequently, intermediates of formula (VIII-a) may be reacted with an intermediate of formula (IV) to prepare intermediates of formula (II) wherein $R^1$ is defined as —CH($R^{1a}$)$_2$, said intermediates being represented by formula (II-a).

Said intermediates of formula (II-a) may also be prepared by first reacting intermediate (IX-d) with intermediate (IV) in the presence of a suitable base to form an intermediate of formula (XII), which may subsequently be deprotected. These reactions and those performed in scheme 1 may all be conducted following conventional methods that are generally known in the art.

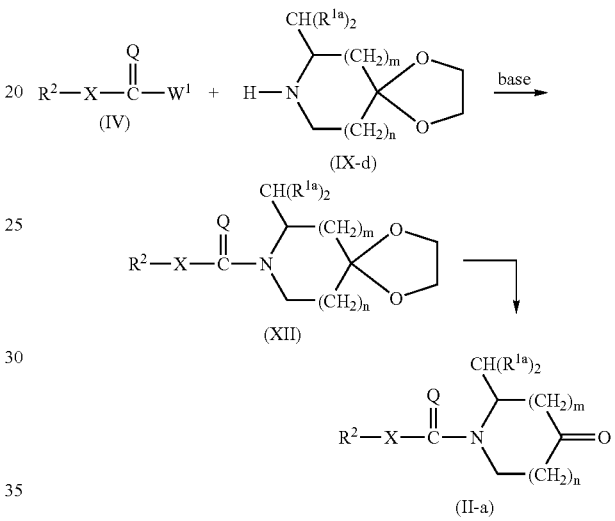

Intermediates of formula (V) may suitably be prepared by reacting an intermediate of formula (VIII-1), being a pro-

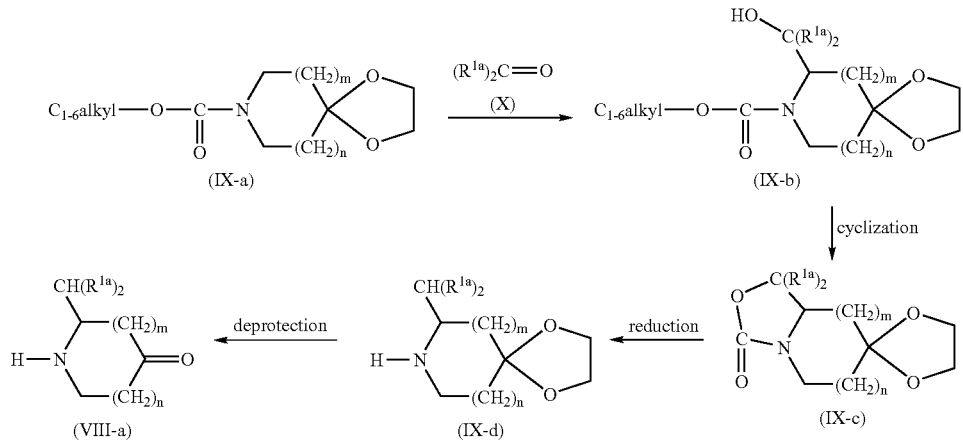

In scheme 1, the intermediates of formula (IX-b) may be prepared by reacting an intermediate of formula (IX-a) with an aldehyde or a ketone of formula (X). The $C_{1-6}$alkylcarbamate moiety in the intermediates of formula (IX-b) may be convened into a fused oxazolone which in turn may be tected intermediate of formula (VIII) with a protecting group $P^2$ such as, for example, a $C_{1-6}$alkyloxycarbonyl group, with an intermediate of formula (III) according to the previously described reductive N-alkylation procedure, and subsequently deprotecting the thus formed intermediate.

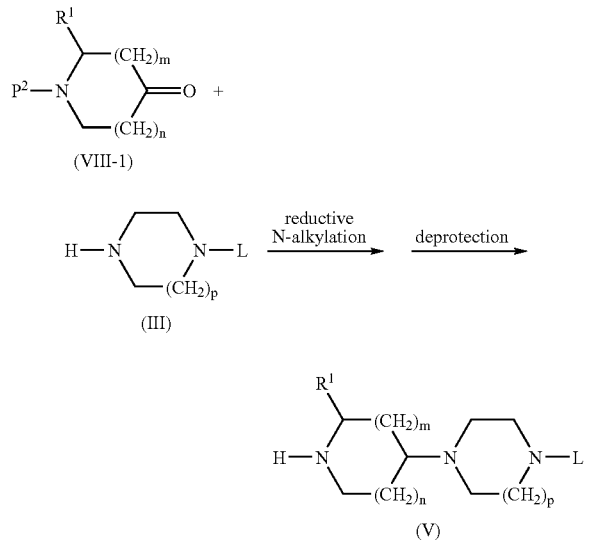

In particular, intermediates of formula (V) wherein $R^1$ is —$CH(R^{1a})_2$, said intermediates being represented by formula (V-a), may be prepared as is depicted in scheme 2.

A. Preparation of the Intermediate Compounds

EXAMPLE A1 a. Preparation of intermediate compound 1

Et$_3$N (0.55 mol) was added to a stirring mixture of 7-(phenylmethyl)-1,4-dioxa-8-azaspiro[4.5]decane (0.5 mol) in toluene (1500 ml). 3,5-Bis(trifluoromethyl)benzoyl chloride (0.5 mol) was added over a 1-hour period (exothermic reaction). The mixture was stirred at room temperature for 2 hours, then allowed to stand for the weekend and washed three times with water (500 ml, 2×250 ml). The organic layer was separated, dried, filtered and the solvent was evaporated. Yielding: 245 g (100%). Part of this fraction was crystallized from petroleum ether. The precipitate was filtered off and dried. Yielding: 1.06 g of intermediate compound 1.

Scheme 2

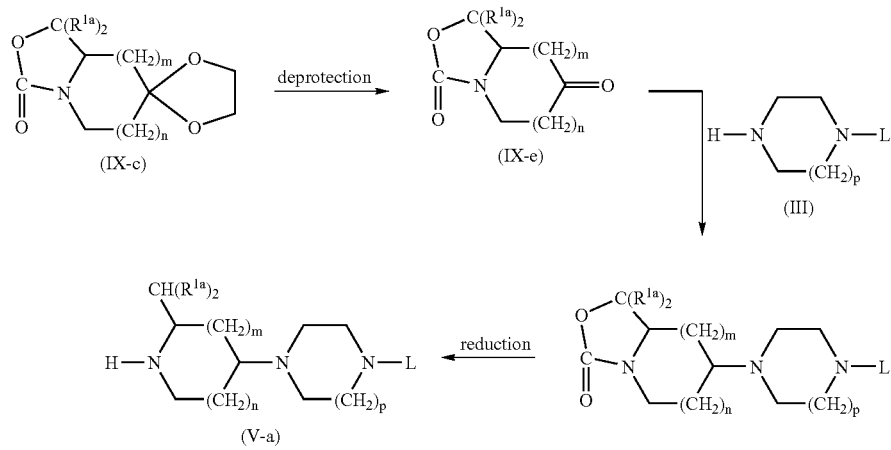

The ketalized intermediate of formula (IX-c) may be transformed to the corresponding ketone of formula (IX-e) which subsequently may be reductively aminated with a piperazine- or homopiperazine derivative of formula (III). The thus obtained intermediate may then be reduced with a suitable reducing agent to an intermediate of formula (V-a).

The following examples are intended to illustrate but not to limit the scope of the present invention.

Experimental Part

Hereinafter "RT" means room temperature, "THF" means tetrahydrofuran, "DIPE" means diisopropylether, "DCM" means dichloromethane and "DMF" means N,N-dimethylformamide.

b. Preparation of intermediate compound 2

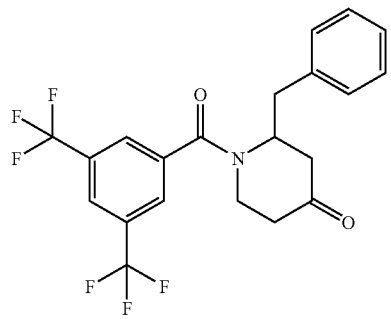

HCl cp (300 ml) was added to a mixture of intermediate compound 1 (0.5 mol) in ethanol (300 ml) and H$_2$O (300 ml). The reaction mixture was stirred at 60° C. for 20 hours. The precipitate was filtered off, ground, stirred in H$_2$O, filtered off, washed with petroleum ether and dried. Yielding: 192 g of intermediate compound 2 ((+-)-1-[3,5-bis(trifluoromethyl)benzoyl]-2-(phenylmethyl)-4-piperidinone) (89.4%) (mixture of R and S enantiomers).

c. Preparation of intermediate compound 3

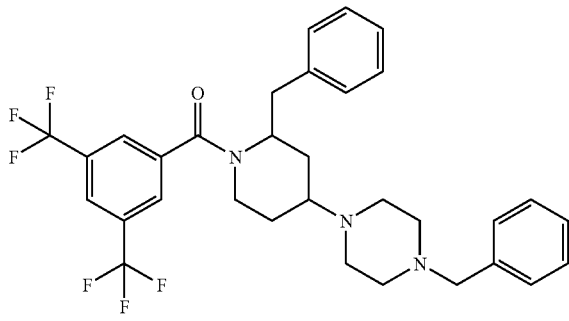

A mixture of intermediate compound 2 (0.046 mol), 1-(phenylmethyl)piperazine (0.051 mol) and Ti-diisopropyloxide (0.056 mol) was stirred for 2 hours at 40° C. The reaction mixture was cooled to room temperature. Ethanol, p.a. (350 ml) was added. NaBH$_4$ (0.138 mol) was added. The resulting reaction mixture was stirred for one hour at room temperature, then for one hour at 50° C. More NaBH$_4$ (5.2 g) was added and the reaction mixture was stirred for 2 hours at 50° C. Again, NaBH$_4$ was added and the reaction mixture was stirred overnight at room temperature, then for 2 hours at 50° C. Water (10 ml) was added. The mixture was stirred for 15 min. CH$_2$Cl$_2$ (200 ml) was added and the mixture was stirred for 15 min. The organic phase was separated, dried (MgSO$_4$), dicalite was added, the mixture was filtered over dicalite, and the filtrate was evaporated. This fraction was separated into (CIS) and (TRANS) by column chromatography over silica gel. The desired (TRANS)-fractions were collected and the solvent was evaporated, giving 14.8 g of residue ((I), 1.06% (CIS)) and 4.9 g of residue ((II), 6% (CIS)). Resolution and purification of those (TRANS)-fractions (±20 g in total) was obtained by chromatography over stationary phase Chiralcel OD (1900Gr) in Prochrom LC110 35 bar (eluent: hexane/ethanol 90/10). The desired fractions were collected and the solvent was evaporated. Yielding: 9.5 g of intermediate compound 3 (2R-trans)-1-[3,5-bis(trifluoromethyl)benzoyl]-2-(phenylmethyl)-4-[4-(phenylmethyl)-1-piperazinyl]piperidine.

d. Preparation of intermediate compound 4

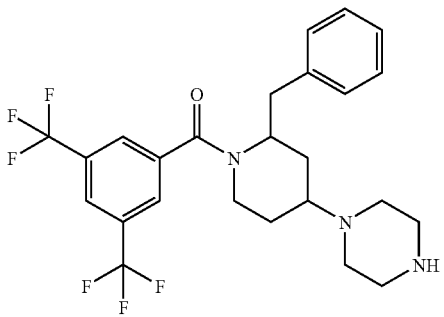

A solution of intermediate compound 3 (0.288 mol) in methanol (700 ml) was hydrogenated at 40° C. with Pd/C, 10% (5 g) as a catalyst. After uptake of H$_2$ (1 equiv), the catalyst was filtered off and the filtrate was evaporated. Yielding: 141.2 g of intermediate compound 4 (+)-(2R-trans)-1-[3,5-bis(trifluoromethyl)benzoyl]-2-(phenylmethyl)-4-(1-piperazinyl)piperidine.

B. Preparation of the Final Compounds

Example B1 a) Preparation of final compound 1

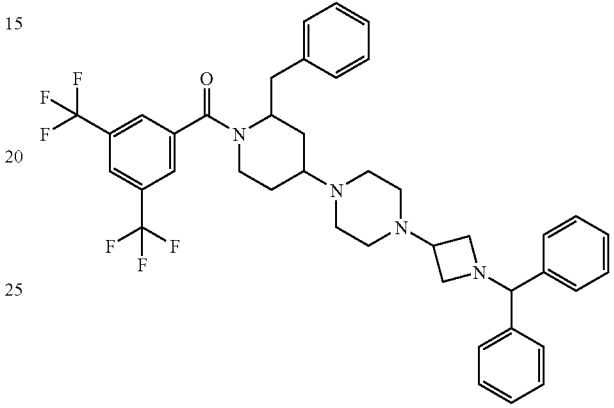

A mixture of 1-(diphenylmethyl)-3-azetidinyl methanesulfonate (0.055 mol), intermediate compound 4 (0.05 mol) and sodium carbonate (0.06 mol) in 4-methyl-2-pentanone (1000 ml) was stirred and refluxed for 18 hours. The mixture was poured out into water. The layers were separated. The aqueous phase was re-extracted with 4-methyl-2-pentanone. The combined organic layers were dried (MgSO$_4$), filtered and the solvent was evaporated. The residue was purified by column chromatography over silica gel (eluent: CH$_2$Cl$_2$/CH$_3$OH from 97/3 to 93/7). The product fractions were collected and the solvent was evaporated. The residue was purified by column chromatography over silica gel (eluent: CH$_2$Cl$_2$/CH$_3$OH from 100/0 to 90/10). The desired fractions were collected and the solvent was evaporated. Yield: 13.7 g of final compound 1 (35%).

b) Preparation of final compound 2

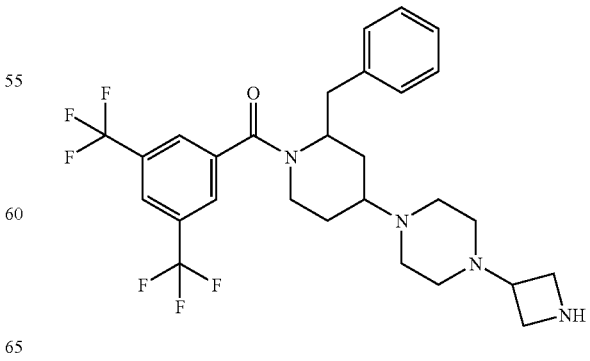

A solution of final compound 1 (0.0183 mol) in methanol (250 ml) was hydrogenated for one week at room temperature with Pd/C 10% (2 g) as a catalyst. After uptake of hydrogen (1 equiv), the catalyst was filtered off and the filtrate was evaporated. The residue was purified by column chromatography over silica gel (eluent: $CH_2Cl_2/CH_3OH/NH_3$) from 100/0 to 85/15). The product fractions were collected and the solvent was evaporated. Yield: 7.5 g of final compound 2 (74%).

c) Preparation of final compound 3

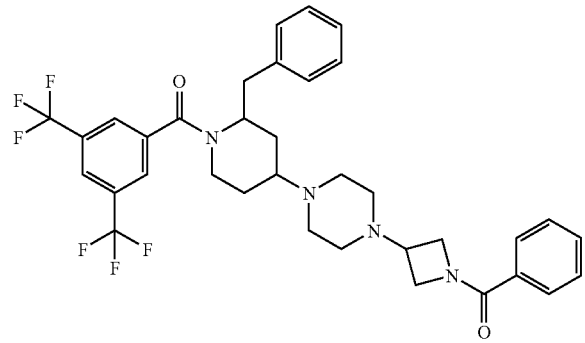

A mixture of final compound 2 (0.002 mol) and triethylamine (0.005 mol) in $CH_2Cl_2$ (50 ml) was stirred at room temperature. A solution of benzoyl chloride (0.0024 mol) in $CH_2Cl_2$ was added dropwise and the resulting reaction mixture was stirred for one hour at room temperature. The mixture was poured out into 1 N NaOH and the mixture was stirred for 20 min. at room temperature. The layers were separated. The aqueous layer was re-extracted with $CH_2Cl_2$. The separated organic layer was washed with water, dried ($MgSO_4$), filtered and the solvent evaporated. The residue was purified by column chromatography over silica gel (eluent: $CH_2Cl_2/CH_3OH$ from 100/0 to 90/10). The product fractions were collected and the solvent was evaporated. Yield: 0.842 g of final compound 3 (64%).

Example B2 Preparation of final compound 19

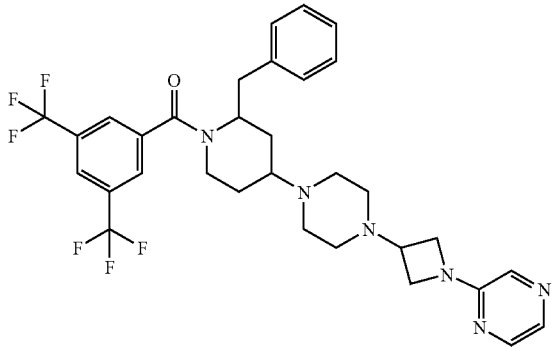

A mixture of final compound 2 (prepared according to B1.b (0.0012 mol), 2-chloropyrazine (0.0024 mol) and $K_2CO_3$ (0.0036 mol) in $CH_3CN$ (50 ml) was stirred and refluxed. Then the solvent was evaporated. The residue was taken up in $H_2O/CH_2Cl_2$ and the separated aqueous layer was extracted with $CH_2Cl_2$. The organic layer was dried ($MgSO_4$), filtered off and the solvent was evaporated. The residue was purified by column chromatography over silica gel (gradient eluent: $CH_2Cl_2/CH_3OH$ 100/0->90/10). The product fractions were collected and the solvent was evaporated. Yield: 0.304 g of final compound 19 (40%).

Example B3 Preparation of final compound 8

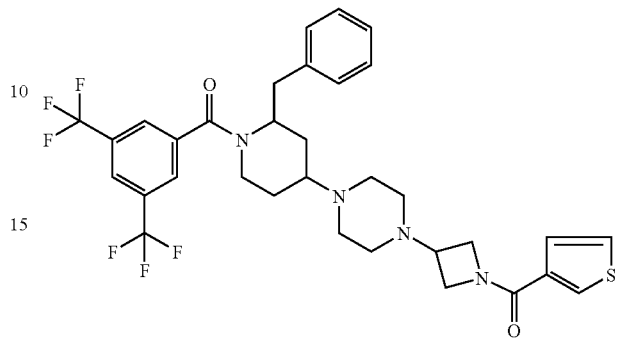

A mixture of 3-thiophenecarboxylic acid (0.00188 mol), N,N-dimethyl-4-pyridinamine (0.00253 mol) and $Et_3N$ (0.01 mol) in $CH_2Cl_2$ (100 ml) was stirred at room temperature. N'(ethylcarbonimidoyl)-N,N-dimethyl-1,3-propanediamine (0.00253 mol) was added portionwise and the mixture was stirred for 1 hour at room temperature. Final compound 2 (prepared according to B1.b) (0.00188 mol) was dissolved in $CH_2Cl_2$ and added dropwise to the mixture. The reaction mixture was stirred overnight at room temperature, poured out into NaOH (1 N in $H_2O$) and stirred for 10 minutes. The layers were separated. The separated aqueous layer was re-extracted with $CH_2Cl_2$. The combined organic layers were washed with $H_2O$, dried ($MgSO_4$), filtered and the solvent was evaporated. The residue was purified by column chromatography over silica gel (gradient eluent: $CH_2Cl_2/CH_3OH$ from 100/0 to 90/10). The desired fractions were collected and the solvent was evaporated. Yield: 0.717 g of final compound 8 (58%).

Example B4 Preparation of final compound 15

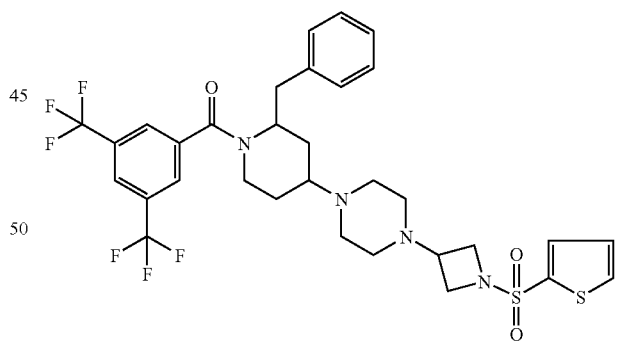

A mixture of final compound 2 (prepared according to B1.b) (0.0012 mol) and $Et_3N$ (0.01 mol) in $CH_2Cl_2$, p.a. (50 ml) was stirred at room temperature, then a solution of 2-thiophenesulfonyl chloride (0.0015 mol) in $CH_2Cl_2$, p.a. was added dropwise and the reaction mixture was stirred for 1 hour at room temperature. NaOH (1N, 20 ml) was added, the resulting mixture was stirred for 10 min. at room temperature and then the layers were separated. The aqueous layer was extracted with $CH_2Cl_2$; the organic layer was washed with $H_2O$, dried ($MgSO_4$), filtered off and the solvent was evaporated. The residue was purified by column chromatography over silica gel (gradient eluent: $CH_2Cl_2/CH_3OH$ from 100/0 to 90/10). The product fractions were collected and the solvent was evaporated. Yield: 0.363 g of final compound 15 (43%).

Example B5 Preparation of final compound 11

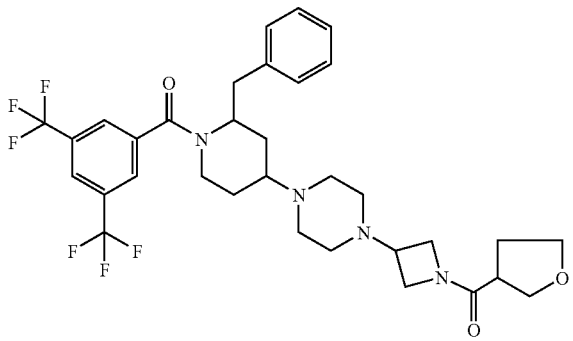

A mixture of (R)-tetrahydro-3-furancarboxylic acid (0.0015 mol), 1-hydroxy-1H-benzotriazole (0.0015 mol) and Et$_3$N (0.0015 mol) in CH$_2$Cl$_2$, p.a. (50 ml) was stirred at room temperature, then N'-(ethylcarbonimidoyl-N,N-dimethyl-1,3-propanediamine (0.0015 mol) was added and the resulting mixture was stirred for 10 min. at room temperature. A solution of final compound 2 (prepared according to B1.b) (0.0012 mol) in CH$_2$Cl$_2$, p.a. was added dropwise and the reaction mixture was stirred overnight at room temperature. H$_2$O and NaHCO$_3$ were added, the mixture was stirred for 10 min. at room temperature and then the layers were separated. The aqueous layer was extracted with CH$_2$Cl$_2$; the organic layer was washed with H$_2$O, dried (MgSO$_4$), filtered off and the solvent was evaporated. The residue was purified by column chromatography over silica gel (gradient eluent: CH$_2$Cl$_2$/CH$_3$OH from 100/0 to 90/10). The product fractions were collected and the solvent was evaporated. Yield: 0.231 g of final compound 11 (29%)

Table 1 lists the compounds of Formula (I) which were prepared according to one of the above described examples.

TABLE 1

| Comp. No. | Exp. No. | Alk$^a$ | Y | Alk$^b$ | L | Physical data |
|---|---|---|---|---|---|---|
| 2 | B1b | cb | cb | cb | H | 2R-trans |
| 19 | B2 | cb | cb | cb | (pyrazinyl) | 2R-trans |
| 1 | B1a | (CH(phenyl)) | cb | cb | (phenyl) | 2R-trans |
| 17 | B1c | cb | C=O | cb | (tert-butyl) | 2R-trans |
| 3 | B1c | cb | C=O | cb | (phenyl) | 2R-trans |

TABLE 1-continued
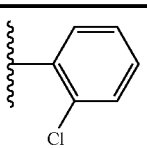
| Comp. No. | Exp. No. | Alk$^a$ | Y | Alk$^b$ | L | Physical data |
|---|---|---|---|---|---|---|
| 18 | B1c | cb | C=O | cb | 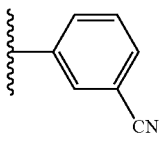 | 2R-trans |
| 4 | B1c | cb | C=O | cb | 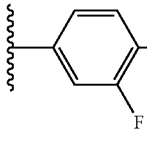 | 2R-trans |
| 5 | B1c | cb | C=O | cb | 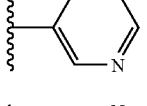 | 2R-trans |
| 6 | B1c | cb | C=O | cb | 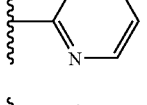 | 2R-trans |
| 20 | B2 | cb | C=O | cb | 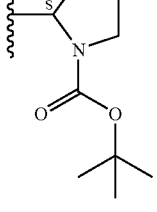 | 2R-trans |
| 21 | B5 | cb | C=O | cb | 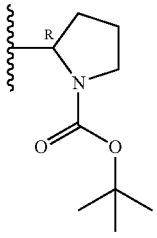 | 2R-trans |
| 22 | B5 | cb | C=O | cb | | 2R-trans |

TABLE 1-continued
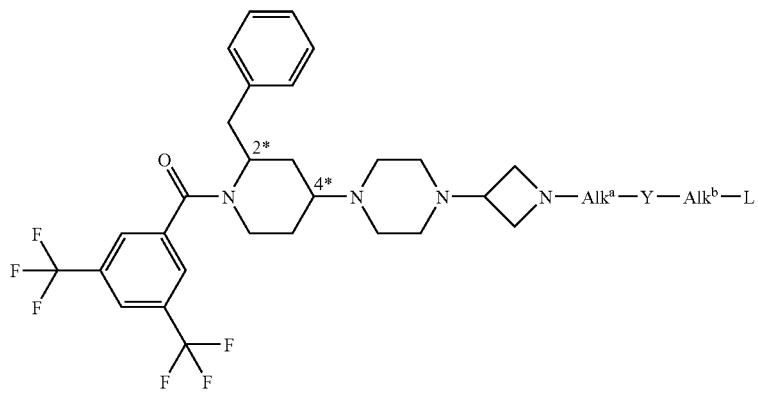
| Comp. No. | Exp. No. | Alkᵃ | Y | Alkᵇ | L | Physical data |
|---|---|---|---|---|---|---|
| 7 | B1c | cb | C=O | cb | 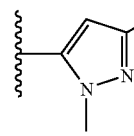 | 2R-trans |
| 8 | B1c | cb | C=O | cb | 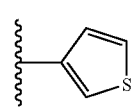 | 2R-trans |
| 11 | B5 | cb | C=O | cb | 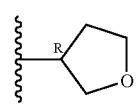 | 2R-trans |
| 12 | B5 | cb | C=O | cb | 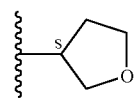 | 2R-trans |
| 9 | B3 | cb | C=O | cb | 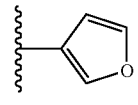 | 2R-trans |
| 16 | B1c | cb | C=O | cb | 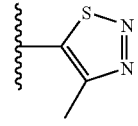 | 2R-trans |
| 10 | B1c | cb | C=O | cb | 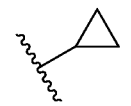 | 2R-trans |
| 14 | B1c | cb | C=O | 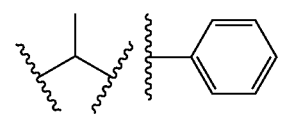 | | 2R-trans |
| 13 | B5 | cb | C=O | 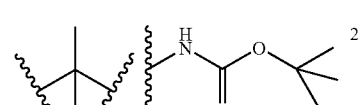 | | 2R-trans |

TABLE 1-continued

| Comp. No. | Exp. No. | Alk^a | Y | Alk^b | L | Physical data |
|---|---|---|---|---|---|---|
| 15 | B4 | cb | O=S=O | cb | thiophene | 2R-trans | cb = covalent bond

C. Analytical Data

For a number of compounds, either melting points, LCMS data or optical rotations were recorded.

1. Melting Points

If possible, melting points (or ranges) were obtained with a Büchi melting point apparatus B-545. The heating medium is a metal block. The melting of the sample is visually observed by a magnifying lens and a big light contrast. Melting points are measured with a temperature gradient of either 3 or 10 degrees Celsius/minute.

TABLE 2

Melting points for selected compounds.

| Compound no. | Result (° C.) |
|---|---|
| 14 | 83.1-91.5° C. |
| 15 | 84.8-92.6° C. |
| 16 | 82.8-97.1° C. |
| 17 | 82.3-90.6° C. |
| 18 | 94.5-103.9° C. |
| 19 | 77.1-99.4° C.) |
| 20 | 88.3-98.4° C. |
| 21 | 100.8-111.2° C. |
| 22 | 99.6-108.2° C. |

2. LCMS Conditions (2 Methods)

The HPLC gradient was supplied by a Waters Alliance HT 2790 system with a columnheater set at 40° C. Flow from the column was split to a Waters 996 photodiode array (PDA) detector and a Waters-Micromass ZQ mass spectrometer with an electrospray ionization source operated in positive and negative ionization mode. Reversed phase HPLC was carried out on a Xterra MS C18 column (3.5 μm, 4.6×100 mm) with a flow rate of 1.6 ml/min. Three mobile phases (mobile phase A 95% 25 mM ammoniumacetate+5% acetonitrile; mobile phase B: acetonitrile; mobile phase C: methanol) were employed to run a gradient condition from 100% A to 50% B and 50% C in 10 min(method 1)/6.5 min (method 2)., to 100% B in 1 min, 100% B for 3 min (method 1)/1 min (method 2). and reequilibrate with 100% A for 2.5 min (method 1)/1.5 min (method 2). An injection volume of 10 μL was used.

Mass spectra were acquired by scanning from 100 to 1000 in 1 s using a dwell time of 0.1 s. The capillary needle voltage was 3 kV and the source temperature was maintained at 140° C. Nitrogen was used a the nebulizer gas. Cone voltage was 10 V for positive ionzation mode and 20 V for negative ionization mode. Data acquisition was performed with a Waters-Micromass MassLynx-Openlynx data system.

TABLE 3

LCMS parent peak and retention time for selected compounds.

| Co. no. | LCMS MS(MH+) Meth. A | Retention time | Method |
|---|---|---|---|
| 1 | 721 | 10.57 | 1 |
| 2 | 555 | 8.03 | 1 |
| 3 | 659 | 5.85 | 2 |
| 4 | 684 | 5.72 | 2 |
| 5 | 695 | 9.69 | 1 |
| 6 | 660 | 5.45 | 2 |
| 7 | 677 | 5.69 | 2 |
| 8 | 665 | 5.76 | 2 |
| 9 | 649 | 9.15 | 1 |
| 10 | 623 | 5.39 | 2 |
| 11 | 653 | 5.46 | 2 |
| 12 | 653 | 5.44 | 2 |
| 13 | 740 | 5.89 | 2 |

D. Pharmacological Example

EXAMPLE D.1

Binding Experiment for h-$NK_1$ h-$NK_2$ and h-$NK_3$ Receptors

The compounds according to the invention were investigated for interaction with various neurotransmitter receptors, ion channels and transporter binding sites using the radioligand binding technique. Membranes from tissue homogenates or from cells, expressing the receptor or transporter of interests, were incubated with a radioactively labelled substance ([$^3$H]- or [$^{125}$I] ligand) to label a particular receptor. Specific receptor binding of the radioligand was distinguished from the non-specific membrane labelling by selectively inhibiting the receptor labelling with an unlabelled drug (the blank), known to compete with the radioligand for binding to the receptor sites. Following incubation, labelled membranes were harvested and rinsed with excessive cold buffer to remove non-bound radioactivity by rapid filtration under suction. Membrane bound radioactivity was counted in a scintillation counter and results were expressed in counts per minute (cpm).

The compounds were dissolved in DMSO and tested at 10 concentrations ranging from $10^{-10}$ to $10^{-5}$ M.

The ability of the compounds according to the invention to displace [$^3$H]-Substance P from cloned human h-NK$_1$ receptors expressed in CHO cells, to displace [$^3$H]-SR-48968 from cloned human h-NK$_2$ receptors expressed in Sf9 cells, and to displace [$^3$H]-SR-142801 from cloned human h-NK$_3$ receptors expressed in CHO cells was evaluated.

EXAMPLE D.2

Signal Transduction (ST)

This test evaluates in vitro functional NK$_1$, NK$_2$ and NK$_3$ antagonistic activity. For the measurements of intracellular Ca$^{++}$ concentrations the cells were grown on 96-well (black wall/transparent bottom) plates from Costar for 2 days until they reached confluence. The cells were loaded with 2 μM Fluo3 in DMEM containing 0.1% BSA and 2.5 mM probenecid for 1 h at 37° C. They were washed 3× with a Krebs buffer (140 mM NaCl, 1 mM MgCl$_2$×6H$_2$O, 5 mM KCl, 10 mM glucose, 5 mM HEPES; 1.25 mM CaCl$_2$; pH 7.4) containing 2.5 mM probenecid and 0.1% BSA (Ca$^{++}$-buffer). The cells were preincubated with a concentration range of antagonists for 20 min at RT and Ca$^{++}$-signals after addition of the agonists were measured in a Fluorescence Image Plate Reader (FLIPR from Molecular Devices, Crawley, England). The peak of the Ca$^{++}$-transient was considered as the relevant signal and the mean values of corresponding wells were analysed as described below.

The sigmoidal dose response curves were analysed by computerised curve-fitting, using the GraphPad Program. The EC$_{50}$-value of a compound is the effective dose showing 50% of maximal effect. For mean curves the response to the agonist with the highest potency was normalised to 100%. For antagonist responses the IC$_{50}$-value was calculated using non-linear regression.

The pIC$_{50}$ data for the signal transduction testing for a representative selection of compounds are presented in Table 4. The last colums indicates—without being limited thereto—for which action the compounds might be most suitable. Of course, since for some neurokinin receptors no data was determined, it is obvious that these compounds might be attributed to another suitable use.

TABLE 4

Pharmacological data for the signal transduction for selected compounds (n.d. = determined).

| Co. No. | pIC$_{50}$ h-NK$_1$ | pIC$_{50}$ h-NK$_2$ | pIC$_{50}$ h-NK$_3$ | Suitable for |
|---|---|---|---|---|
| 16 | 8.13 | 5 | 5.31 | NK1 |
| 11 | 7.98 | 5 | 5 | NK1 |
| 18 | 7.98 | 5 | 5.36 | NK1 |
| 17 | 7.96 | 5 | 5.26 | NK1 |
| 3 | 7.71 | n.d. | n.d. | NK1 |
| 13 | 7.47 | 5 | 5 | NK1 |
| 21 | 7.46 | 5.71 | 5.44 | NK1 |
| 22 | 7.43 | 5.26 | 5.74 | NK1 |
| 20 | 7.38 | 5 | 5.09 | NK1 |
| 12 | 7.36 | 5 | 5 | NK1 |
| 19 | 7.34 | 5 | 5 | NK1 |
| 4 | 7.34 | n.d. | n.d. | NK1 |
| 6 | 7.31 | n.d. | n.d. | NK1 |
| 9 | 7.26 | n.d. | n.d. | NK1 |
| 10 | 7.2 | n.d. | n.d. | NK1 |
| 7 | 7.14 | n.d. | 5.46 | NK1 |
| 5 | 6.99 | n.d. | n.d. | NK1 |
| 2 | 6.91 | n.d. | n.d. | NK1 |
| 8 | 6.69 | n.d. | n.d. | NK1 |
| 14 | 7.64 | 5.4 | 6.2 | NK1/NK3 |
| 15 | 7.49 | 5.26 | 5.91 | NK1/NK3 |

E. Composition Examples

"Active ingredient" (A.I.) as used throughout these examples relates to a compound of Formula (I), the pharmaceutically acceptable acid or base addition salts thereof, the stereochemically isomeric forms thereof, the N-oxide form thereof and prodrugs thereof.

EXAMPLE E.1

Oral Drops

500 Grams of the A.I. was dissolved in 0.5 l of 2-hydroxypropanoic acid and 1.5 l of the polyethylene glycol at 60–80° C. After cooling to 30–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE E.2

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE E.3

Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE E.4

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

The invention claimed is:

1. A compound according to the general Formula (I)

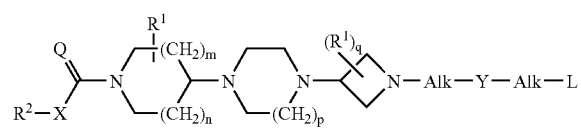

the pharmaceutically acceptable acid or base addition salts thereof, the stereochemically isomeric forms thereof, the N-oxide form thereof and prodrugs thereof, wherein:

n is an integer, equal to 1;
m is an integer, equal to 1;
p is an integer equal to 1;
q is an integer equal to 0;
Q is O;
X is a covalent bond;
$R^1$ is $Ar^1$ or $Ar^1$-alkyl;
$R^2$ is $Ar^2$;
Y is a covalent bond or a bivalent radical of formula —C(=O)— or —$SO_2$—;
each Alk is independently from each other, a covalent bond; a bivalent straight, saturated hydrocarbon radical having from 1 to 6 carbon atoms; or a cyclic saturated or unsaturated hydrocarbon radical having from 3 to 6 carbon atoms; each radical optionally substituted on one or more carbon atoms with one or more phenyl radicals;
L is hydrogen, alkyl, mono- or di(alkyloxycarbonyl) amino, $Ar^3$, or $Het^2$;
$Ar^1$ is phenyl;
$Ar^2$ is phenyl, optionally substituted with 1, 2 or 3 alkyl substituents which can be substituted with one or more halo radicals;
$Ar^3$ is phenyl, optionally substituted with 1 or 2 substituents, each independently halo or cyano;
$Het^2$ is a monocyclic heterocyclic radical that is pyrrolidinyl, tetrahydrofuranyl, pyrazolyl, furanyl, thienyl, thiadiazolyl, pyridinyl or pyrimidinyl, each radical optionally substituted with one or more alkyl or alkyloxycarbonyl radicals; and
alkyl is a straight saturated hydrocarbon radical having from 1 to 6 carbon atoms or a cyclic saturated hydrocarbon radicals having from 3 to 6 carbon.

2. A compound according to claim 1 wherein $R^1$ is $Ar^1$ methyl and attached to the 2-position or $R^1$ is $Ar^1$ and attached to the 3-position.

3. A compound according to claim 1 wherein the $R^2$—X—C(=Q)-moiety is 3,5-di-(trifluoromethyl) phenylcarbonyl.

4. A compound according to claim 1 wherein Y is —C(=O)—.

5. A compound according to claim 1 wherein Alk is a covalent bond.

6. A compound according to claim 1 wherein L is $Het^2$.

7. A compound that is (2R-trans) [4-(4-azetidin-3-yl-piperazin-1-yl)-2-benzyl-piperidin-1-yl]-(3,5-bis-trifluoromethyl-phenyl)-methanone;

(2R-trans){4-[4-(1-benzoyl-azetidin-3-yl)-piperazin-1-yl]-2-benzyl -piperidin-1-yl}-(3,5-bis-trifluoromethyl-phenyl)-methanone;

(2R-trans)3-(3-{4-[2-benzyl-1-(3,5-bis-trifluoromethyl-benzoyl)-piperidin-4-yl]-piperazin-1-yl}-azetidine-1-carbonyl)-benzonitrile;

(2R-trans)(2-benzyl-4-{4-[1-(3,4-difluoro-benzoyl)-azetidin-3-yl]-piperazin-1-yl}-piperidin-1 -yl)-(3,5-bis-trifluoromethyl-phenyl)-methanone;

(2R-trans)(2-benzyl-4-{4-[1-(pyridine-3-carbonyl)-azetidin-3-yl]-piperazin-1-yl}-piperidin-1-yl)-(3,5-bis-trifluoromethyl-phenyl)-methanone;

(2R-trans)(2-benzyl-4-{4-[1-(2,5-dimethyl-2H-pyrazole-3-carbonyl)-azetidin-3-yl]-piperazin-1-yl}-piperidin-1-yl)-(3,5-bis-trifluoromethyl-phenyl)-methanone;

(2R-trans)(2-benzyl-4-{4-[1-(thiophene-3-carbonyl)-azetidin-3-yl]-piperazin-1-yl}-piperidin-1-yl)-(3,5-bis-trifluoromethyl-phenyl)-methanone;

(2R-trans)(2-benzyl-4-{4-[1-(furan-3-carbonyl)-azetidin-3-yl]-piperazin-1-yl}-piperidin-1-yl)-(3,5-bis-trifluoromethyl-phenyl)-methanone;

(2R-trans){2-benzyl-4-[4-(1-cyclopropanecarbonyl-azetidin-3-yl)-piperazin-1-yl]-piperidin-1-yl}-(3,5-bis-trifluoromethyl-phenyl)-methanone;

(2R-trans)(2-benzyl-4-{4-[1-((3R) tetrahydro-furan-3-carbonyl)-azetidin-3-yl]-piperazin-1-yl}-piperidin-1-yl)-(3,5-bis-trifluoromethyl-phenyl)-methanone;

(2R-trans)(2-benzyl-4-{4-[1-((3S)tetrahydro-furan-3-carbonyl)-azetidin-3 -yl]-piperazin-1-yl}-piperidin-1-yl)-(3,5-bis-trifluoromethyl-phenyl)-methanone;

(2R-trans) [2-(3-{4-[2-benzyl-1-(3,5-bis-trifluoromethyl-benzoyl) -piperidin-4-yl]-piperazin-1-yl}-azetidin-1-yl)-1,1-dimethyl-2-oxo-ethyl-carbamic acid tert-butyl ester;

(2R-trans) 1-(3-{4-[2-benzyl-1-(3,5-bis-trifluoromethyl-benzoyl) -piperidin-4-yl]-piperazin-1-yl}-azetidin-1-yl)-2-phenyl-propan-1-one;

(2R-trans)(2-benzyl-4-{4-[1-(thiophene-2-sulfonyl)-azetidin-3-yl]-piperazin-1-yl}-piperidin-1-yl)-(3,5-bis-trifluoromethyl-phenyl)-methanone;

(2R-trans)(2-benzyl-4-{4-[1-(4-methyl-[1,2,3]thiadiazole-5-carbonyl)-azetidin-3-yl]-piperazin-1-yl}-piperidin-1-yl)-(3,5-bis-trifluoromethyl-phenyl)-methanone;

(2R-trans)1-(3-{4-[2-benzyl-1-(3,5-bis-trifluoromethyl-benzoyl)-piperidin -4-yl]-piperazin-1-yl}-azetidin-1-yl)-2,2-dimethyl-propan-1-one;

(2R-trans)(2-benzyl-4-{4-[1-(2-chloro-benzoyl)-azetidin-3-yl]-piperazin-1-yl}-piperidin-1-yl)-(3,5-bis-trifluoromethyl-phenyl)-methanone;

(2R-trans){2-benzyl-4-[4-(1-pyrazin-2-yl-azetidin-3-yl)-piperazin-1-yl]-piperidin-1-yl}-(3,5 -bis-trifluoromethyl-phenyl)-methanone;

(2R-trans)(2-benzyl-4-{4-[1-(pyrazine-2-carbonyl)-azetidin-3-yl]-piperazin-1-yl}-piperidin-1-yl)-(3,5-bis-trifluoromethyl-phenyl)-methanone;

(2R-trans) 2-(3-{4-[2-benzyl-1-(3,5-bis-trifluoromethyl-benzoyl) -piperidin-4-yl]-piperazin-1-yl}-azetidine-1-carbonyl)-(2R) pyrrolidine-1-carboxylic acid tert-butyl ester; or (2R-trans)2-(3-{4-[2-benzyl-1-(3,5-bis-trifluoromethyl-benzoyl)-piperidin -4-yl]-piperazin-1-yl}-azetidine-1-carbonyl)-(2S) pyrrolidine-1-carboxylic acid tert-butyl ester.

8. A method for treating a patient suffering from schizophrenia, emesis, anxiety, depression, irritable bowel syndrome, circadian rhythm disturbances, pain, neurogenic inflammation, asthma, micturition disorders or nociception, comprising administering to the patient a therapeutically effective amount of a compound according to claim 1.

9. A pharmaceutical composition comprising a pharmaceutically acceptable carrier and, as active ingredient, a therapeutically effective amount of a compound according to claim 1.

10. A process for preparing a pharmaceutical composition comprising mixing a pharmaceutically acceptable carrier with a therapeutically effective amount of a compound of claim 1.

11. A process for the preparation of a compound of Formula (I″) in which an intermediate compound of Formula (II) is reacted with an intermediate compound of Formula (III)

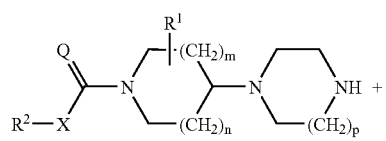

(III)

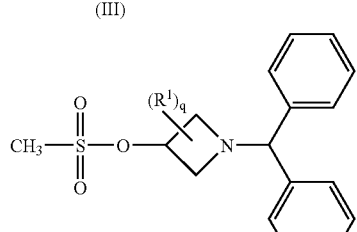

(II)

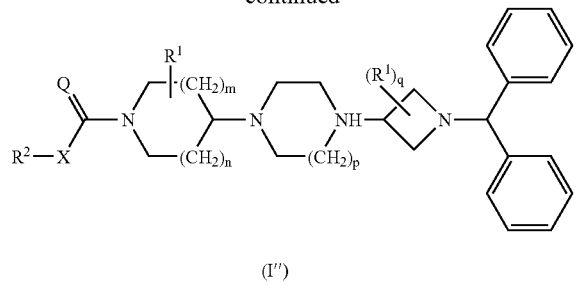

(I″)

wherein
X is a covalent bond;
$R^1$ is $Ar^1$ or $Ar^1$-alkyl, wherein $Ar^1$ is phenyl;
$R^2$ is $Ar^2$ wherein $Ar^2$ is phenyl, optionally substituted with 1, 2 or 3 alkyl substituents which can be substituted with one or more halo radicals;
n is an integer, equal to 1;
m is an integer, equal to 1;
p is an integer equal to 1;
q is an integer equal to 0; and
Q is O.

12. A process for the preparation of a compound of Formula (I′) in which a final compound of Formula (I″) is reductively hydrogenated

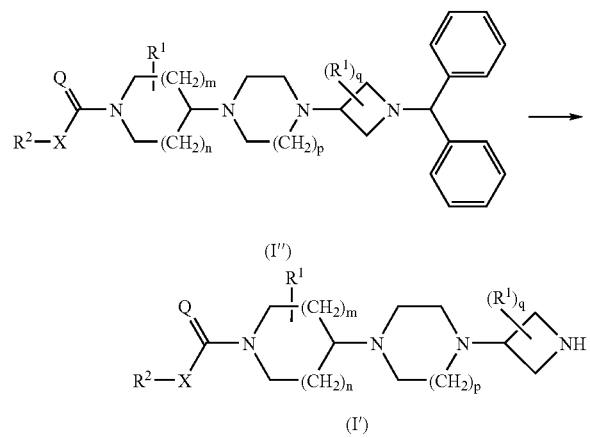

wherein
X is a covalent bond;
$R^1$ is $Ar^1$ or $Ar^1$-alkyl, wherein $Ar^1$ is phenyl;
$R^2$ is $Ar^2$ wherein $Ar^2$ is phenyl, optionally substituted with 1, 2 or 3 alkyl substituents which can be substituted with one or more halo radicals;
n is an integer, equal to 1;
m is an integer, equal to 1;
p is an integer equal to 1;
q is an integer equal to 0; and
Q is O.

13. A process for the preparation of a compound according to Formula (I′) comprising
preparing a compound of Formula (I″) in which an intermediate compound of Formula (II) is reacted with an intermediate compound of Formula (III)

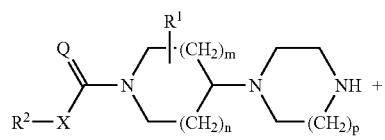

(III)

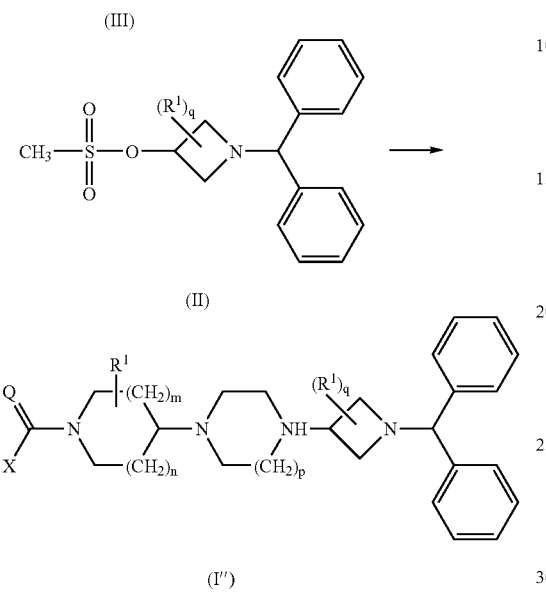

wherein
X is a covalent bond;
R¹ is Ar¹ or Ar¹-alkyl, wherein Ar¹ is phenyl;
R² is Ar², wherein Ar² is phenyl, optionally substituted with 1, 2 or 3 alkyl substituents which can be substituted with one or more halo radicals
n is an integer, equal to 1;
m is an integer, equal to 1;
p is an integer equal to 1;
is an integer equal to 0;
Q is O; and
preparing a compound of Formula (I') in which a final compound of Formula (I") is reductively hydrogenated

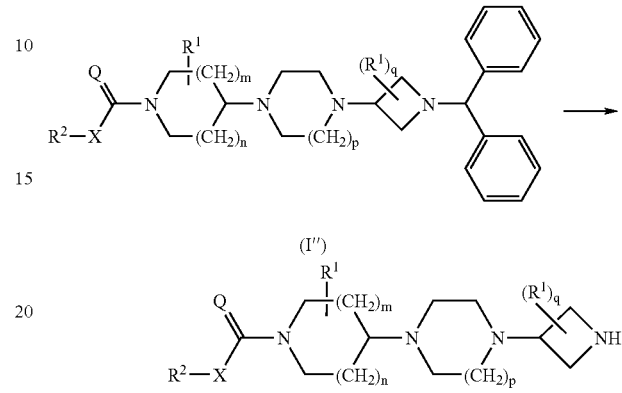

wherein
X is a covalent bond;
R¹ is Ar¹ or Ar¹-alkyl, wherein Ar¹ is phenyl;
R² is Ar², wherein Ar² is phenyl, optionally substituted with 1, 2 or 3 alkyl substituents which can be substituted with one or more halo radicals;
n is an integer, equal to 1;
m is an integer, equal to 1;
p is an integer equal to 1;
q is an integer equal to 0; and
Q is O.

* * * * *